(12) United States Patent
Melander et al.

(10) Patent No.: US 9,815,794 B2
(45) Date of Patent: Nov. 14, 2017

(54) INHIBITION OF BACTERIAL BIOFILMS AND MICROBIAL GROWTH WITH IMIDAZOLE DERIVATIVES

(71) Applicant: North Carolina State University, Raleigh, NC (US)

(72) Inventors: Christian Melander, Raleigh, NC (US); W. Steve McCall, Gimmeldingen (DE); Zhaoming Su, Jupiter, FL (US); Roberta Melander, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 15/019,025

(22) Filed: Feb. 9, 2016

(65) Prior Publication Data

US 2016/0194288 A1 Jul. 7, 2016

Related U.S. Application Data

(63) Continuation of application No. 14/035,020, filed on Sep. 24, 2013, now Pat. No. 9,295,257, which is a continuation of application No. PCT/US2012/030328, filed on Mar. 23, 2012.

(60) Provisional application No. 61/467,555, filed on Mar. 25, 2011, provisional application No. 61/467,547, filed on Mar. 25, 2011.

(51) Int. Cl.
*A01N 59/20* (2006.01)
*A01N 43/50* (2006.01)
*C07D 233/88* (2006.01)

(52) U.S. Cl.
CPC ........... *C07D 233/88* (2013.01); *A01N 43/50* (2013.01); *A01N 59/20* (2013.01)

(58) Field of Classification Search
None
See application file for complete search history.

(56) References Cited

U.S. PATENT DOCUMENTS

| | | | |
|---|---|---|---|
| 3,575,929 | A | 4/1971 | Jones |
| 4,514,382 | A | 4/1985 | Gaffar et al. |
| 5,358,960 | A | 10/1994 | Ulrich et al. |
| 5,670,055 | A | 9/1997 | Yu et al. |
| 5,814,668 | A | 9/1998 | Whittemore et al. |
| 5,834,411 | A | 11/1998 | Bolkan et al. |
| 6,143,774 | A | 11/2000 | Heckmann et al. |
| 7,087,661 | B1 | 8/2006 | Alberte et al. |
| 7,132,567 | B2 | 11/2006 | Alberte et al. |
| 7,160,879 | B2 | 1/2007 | DeSimone et al. |
| 2003/0171421 | A1 | 9/2003 | Davies et al. |
| 2003/0229000 | A1 | 12/2003 | Merritt et al. |
| 2004/0024037 | A1 | 2/2004 | Ryu et al. |
| 2004/0249441 | A1 | 12/2004 | Miller et al. |
| 2005/0161859 | A1 | 7/2005 | Miller et al. |
| 2006/0014285 | A1 | 1/2006 | Eldridge et al. |
| 2006/0018945 | A1 | 1/2006 | Britigan et al. |
| 2006/0228384 | A1 | 10/2006 | Eldridge |
| 2006/0276468 | A1 | 12/2006 | Blow |
| 2007/0231291 | A1 | 10/2007 | Huang et al. |
| 2009/0143230 | A1 | 6/2009 | Melander et al. |
| 2009/0263438 | A1 | 10/2009 | Melander et al. |
| 2009/0270475 | A1 | 10/2009 | Melander et al. |

FOREIGN PATENT DOCUMENTS

| | | | | |
|---|---|---|---|---|
| CA | 6218549 B1 | | 4/2001 | |
| EP | WO 2011/080132 | * | 7/2011 | ........... C07D 233/88 |
| WO | WO 2005/012263 A1 | | 2/2005 | |
| WO | WO 2008/094479 A1 | | 8/2008 | |

OTHER PUBLICATIONS

Nishimura, Tamio. Reaction of Guanidines with α-Diketones. Syntheses of 4,5-Disubstituted-2-aminoimidazoles and 2,6-Unsymmetrically Substituted Imidazo[4,5-d]imidazoles. J. Org. Chem. 44(5), 1979, 818-824.*

Boehm, JC et al. Synthesis and LTB4 receptor antagonist activities of the naturally occurring LTB4 receptor antagonist leucettamine A and related analogues. J. Med. Chem. 1993; 36: 3333-3340.

Su Z et al. A nitroenolate approach to the synthesis of 4,5-disubstituted-2-aminoimidazoles. Pilot library assembly and screening for antibiotic and antibiofilm activity. Organic & Biomolecular Chemistry. 2010; 8: 3814-2822.

Nagai W et al. Synthesis of 2-amino-I-histidine and 2-aminohistamine. Journal of Organic Chemistry. Jan. 1, 1973; 88(11): 1971-1974.

Ballard TE et al. Synthesis and antibody activity of a second-generation reverse-amide oroldin library: a structure-activity relationship study. Chem Eur J. Oct. 22, 2008; 14(34): 10745-10761.

Supplementary European Search Report and Search Opinion, EP 08854205.1, dated May 9, 2014.

Bonner J. Antibiotic combinations tackle resistance. Chemistry World. 2007, http//www.rsc.org/chemistryworld/news/2007/aprll/04040701.asp, retrieved Jan. 11, 2014, 2 pages.

Antimicrobial products in the home: The evolving problem of antibiotic resistance [online]; [retrieved on Jun. 16, 2008] [URL; http://www.cps.ca/english/statements/ID/ID06-02.htm.

Avery S. Slime-fighting molecule may rearm antibiotics, newsobserver.com. The News and Observer. Raleigh, NC. Apr. 22, 2009: 2 pp.

Ballard TE et al. Antibiofilm activity of a diverse oroidin library generated through reductive acylation. J. Org. Chem. 2009; 74(4): 1755-1758.

Ballard TE et al. Synthesis and antiblofilm activity of a second-generation reverse-amide oroidin library: a structure-activity relationship study, Chemistry. 2008; 14(34): 10745-61. Abstract only.

Casalinuovo IA et al. Fluconazole resistance in *Candida albicans*: a review of mechanisms. European Review for Medical and Pharmacological Sciences. 2004; 8(2): 69-77.

(Continued)

*Primary Examiner* — Samantha Shterengarts
(74) *Attorney, Agent, or Firm* — Myers Bigel, P.A.

(57) ABSTRACT

Disclosure is provided for imidazole derivative compounds useful to inhibit the formation of biofilms and/or inhibit microbial growth, compositions including these compounds, devices including these compounds, and methods of using the same.

26 Claims, No Drawings

(56) References Cited

OTHER PUBLICATIONS

Document No. 139:164905 retrieved from CAPLUS on Jan. 3, 2010.
Document No. 62:66837 retrieved from CAPLUS on Jan. 3, 2010.
Document No. 80:15172 retrieved from CAPLUS on Jan. 3, 2010.
Fishing for seafood safety. Scope. North Carolina State University College of Physical and Mathematical Sciences. Fall 2007: 11.
Foley L. and Buchi G. Biomimetic synthesis of dibromophakellin. J. Am. Chem. Soc. (1982), vol. 104, pp. 1776-1777.
Galvin F. Marine inspiration for biofilm break up. Chemical Biology. RCS Publishing. Mar. 5, 2008: 2 pp.
Ginsburg, I. APMIS 2002, 110, pp. 753-770.
Hoffmann H and Lindel T. Synthesis of the pyrrole-imidazolealkaloids. Synthesis. 2003; 12: 1753-1783.
Huigens III R.W., et al. Inhibition of pseudomonas aeruginosa biofilm formation with bromoageliferin analogues. J. Am. Chem. Soc. (2007), vol. 129, pp. 6966-6967.
Huigens RW 3rd et al. Control of bacterial biofilms with marine alkaloid derivatives. Molecular BioSystems, 2008; 4: 614-621.
Huigens RW 3rd et al. Inhibition of Acinetobacter baumannii, *Staphylococcus aureus* and Pseudomonas aeruginosa biofilm formation with a class of TAGE-triazole conjugates. Org. Biomol. Chem. 2009; 7: 794-802.
International Search Report and Written Opinion for PCT/US08/01045, dated May 9, 2008.
International Search Report and Written Opinion, PCT/US09/02101, dated Jul. 13, 2009.
International Search Report and Written Opinion, PCT/US09/02446, dated Aug. 31, 2009.
Kelly SR et al. Effects of Caribbean sponge extracts on bacterial attachment. Aquatic Microbial Ecology. Mar. 13, 2003; 31: 175-182.
Kelly SR et al. Effects of Caribbean sponge secondary metabolites on bacterial colonization. Aquatic Microbial Ecology. Sep. 6, 2005; 40: 191-203.
Lydersen K. Scientists learning to target bacteria where they live. washingtonpost.com. The Washington Post, Mar. 9, 2009; A05: 3 pp.
Melander C et al. Evaluation of dihydrooroidin as an antifouling additive in marine paint. International Biodeterioration & Biodegradation. 2009; 53: 529-532.
Mourabit A. A. and Potier P. Sponge's molecular diversity through the ambivalent reactivity of 2-aminoimidazole: a universal chemical pathway to the oroidin-based pyrrole-imidazole alkaloids and their palau'amine congeners. Eur. J. Org. Chem. (2001), pp. 237-243.
Musk Jr. D.J. and Hergenrother P.J. Chemical countermeasures for the control of bacterial biofilms: effective compounds and promising targets. Current Medicinal Chemistry (2006), vol. 13, pp. 2163-2177.
Rautio J et al. Prodrugs: design and clinical applications. Nature Reviews. Mar. 2008; 7: 255-270.
Rice, L., Biochemical Pharmacology 2006, 71, pp. 991-995.
Richards JJ and Melander C. Controlling bacterial biofilms. ChemBioChem. Epub ahead of print: Aug. 13, 2009; 9 pp.
Richards JJ and Melander C. Synthesis of a 2-aminoimidazole library for antibiofilm screening utilizing the Sonogashira reaction. J. Org. Chem. 2008; 73(13): 5191-5193.
Richards JJ et al. Amide isosteres of oroldln: assessment of antibiofilm activity and *C. elegans* toxicity. Journal of Medicinal Chemistry. 2009; 52(15): 4582-4585.
Richards JJ et al. Effects of N-pyrrole substitution on the antibiofilm activities of oroidin derivatives against Acinetobacter baumannii, Bioorganic & Medicinal Chemistry Letters, 2008; 18: 4325-4327.
Richards JJ et al. Inhibition and dispersion of proteobacterial biofilms. Chem. Comm. 2008; 1698-1700.
Richards JJ et al. Inhibition and dispersion of Pseudomonas aeruginosa biofilms with reverse amide 2-aminoimidazole oroidin analogues. Organic & Biomolecular Chemistry, Apr. 21, 2008; 6(8): 1356-1363.
Richards JJ et al. Synthesis and screening of an oroidin library against Pseudomonas aeruginosa biofilms. ChemBioChem, 2008; 9: 1267-1279.
Rogers SA and Melander C. Construction and screening of a 2-aminoimidazole library identifies a small molecule capable of inhibiting and dispersing bacterial biofilms across order, class, and phylum. Angew. Chem. Int. Ed, 2008; 47: 5229-5231.
Rogers SA et al. A 2-aminobenzimidazole that inhibits and disperses gram-positive biofilms through a zinc-dependent mechanism. J. Am. Chem. Soc. 2009; 131(29): 9868-9869.
Rogers SA et al. Chemical synthesis and biological screening of 2-aminoimidazole-based bacterial and fungal antibiofilm agents. Chembiochem. Feb. 2010; 11: 396-410.
Rogers SA et al. Synergistic effects between conventional antibiotics and 2-aminoimidazole-derived antibiofilm agents. Antimlcrob. Agents Chemother. Mar. 8, 2010: 1-34.
Rogers SA et al. Tandem dispersion and killing of bacteria from a biofilm. Organic & Biomolecular Chemistry. 2009; 7: 603-606.
Salvatori, et al. J Org Chem, 2005, 70 pp. 8208-8211.
Shore D. College Profile: Dr. John Cavanagh shows that in scientific collaboration—as in a community of molecules—the product is more powerful than the sum of its parts. Perspectives Online. North Carolina State University. Summer 2007: 4 pp.
Smith DA, Do prodrugs deliver? Current Opinion in Drug Discovery & Development. 2007; 10(5): 550-559.
Stokstad E. Sponging away antibiotic resistance. Findings. The Science Magazine News Blog. Feb. 14, 2009: 1 p.
Taking the Resistance out of drug-resistant infections. PhysOrg.com. Apr. 10, 2009: 2 pp.
Testa B. Prodrugs: bridging pharmacodynamic/pharmacokinetic gaps. Current Opinion in Chemical Biology. 2009; 13: 338-344.
Wang B et al. Drug delivery: principles and applications. 2005 John Wiley & Sons, Inc. Publication. Section 8.3, pp. 136-137.
Yamada A. et al. Development of chemical substances regulating biofilm formation. Bull. Chem. Soc. Jpn. (1997), No. 70, pp. 3061-3069.
International Search Report and Written Opinion, PCT/US2012/030328, dated Sep. 14, 2012.
PubChem compound CID 46848169 (create date: Aug. 23, 2010) (retrieved from http://pubchem.ncbi.nlm.nih.gov on Jun. 13, 2012), 3 pages.

* cited by examiner

INHIBITION OF BACTERIAL BIOFILMS AND MICROBIAL GROWTH WITH IMIDAZOLE DERIVATIVES

RELATED APPLICATIONS

This application is a continuation under 35 U.S.C. 111(a) of U.S. application Ser. No. 14/035,020, filed Sep. 24, 2013, now allowed, which is a continuation under 35 U.S.C. 111(a) of PCT Application No. PCT/US2012/030328, filed Mar. 23, 2012, which claims the benefit of U.S. Provisional Patent Application Ser. No. 61/467,555, filed Mar. 25, 2011, and U.S. Provisional Patent Application Ser. No. 61/467,547, filed Mar. 25, 2011, the disclosure of each of which is incorporated by reference herein in its entirety.

FIELD OF THE INVENTION

This invention relates to compounds, compositions and methods useful in the control of biofilms and/or microbial growth.

BACKGROUND OF THE INVENTION

Biofilms are complex communities of microorganisms commonly found on a variety of substrates or surfaces that are moist or submerged (Musk et al., *Curr. Med. Chem.*, 2006, 13: 2163; Donlan et al., *Clin. Microbiol. Rev.*, 2002, 15: 167). Though primarily populated by bacteria, biofilms can also contain many different individual types of microorganisms, e.g., bacteria, archaea, protozoa and algae. The formation of biofilms can be thought of as a developmental process in which a few free-swimming (planktonic) bacteria adhere to a solid surface and, in response to appropriate signals, initiate the formation of a complex sessile microcolony existing as a community of bacteria and other organisms. Bacteria within biofilms are usually embedded within a matrix, which can consist of protein, polysaccharide, nucleic acids, or combinations of these macromolecules, and which protects the inhabiting organisms from antiseptics, microbicides, and host cells. It has been estimated, for example, that bacteria within biofilms are upwards of 1,000-fold more resistant to conventional antibiotics (Rasmussen et al., *Int. J. Med. Microbiol.*, 2006, 296: 149).

Biofilms play a significant role in infectious disease. It is estimated that biofilms account for between 50-80% of microbial infections in the body, and that the cost of these infections exceeds $1 billion annually. A few of the diseases in which biofilms have been implicated include endocarditis, otitis media, chronic prostatitis, periodontal disease, chronic urinary tract infections, and cystic fibrosis. Persistent infections of indwelling medical devices also remains a serious problem for patients because eradication of these infections is virtually impossible. The persistence of biofilm populations is linked to their inherent insensitivity to antiseptics, antibiotics, and other antimicrobial compounds or host cells.

Deleterious effects of biofilms are also found in non-medical settings. For example, biofilms are a major problem in the shipping industry. Biofilms form on and promote the corrosion of ship hulls and also increase the roughness of the hulls, increasing the drag on the ships and thereby increasing fuel costs. The biofilms can also promote the attachment of larger living structures, such as barnacles, to the hull. Fuel can account for half of the cost of marine shipping, and the loss in fuel efficiency due to biofilm formation is substantial. One method of controlling biofilms is to simply scrape the films off of the hulls. However, this method is costly and time-consuming, and can promote the spread of troublesome non-native species in shipping waters. Another method involves the use of antifouling coatings containing tin. However, tin-based coatings are now disfavored due to toxicity concerns.

Agricultural production is also adversely affected by microorganisms growth on plants. The five main crops on which modern societies depend most heavily include corn, cotton, rice, soybeans, and wheat. All of these crops are affected in a deleterious manner by biofilm formation. Other valuable plants, such as those producing fruits and vegetables, plants grown for biomass, and forestry crops and ornamentals, are similarly affected. Given the steadily growing global population that is predicted to reach 6-9 billion persons by mid-century, the continual strain on existing and finite agricultural lands, and the recent diversion of valuable agricultural land from production of crops to production of biomass for fuels, new approaches are needed to control microbial effects in plants.

Due to the breadth of detrimental effects caused by bacterial biofilms, there has been an effort to develop small molecules that will inhibit their formation (Musk et al., *Curr. Med. Chem.*, 2006, 13: 2163). The underlying principle is that if bacteria can be maintained in the planktonic state, they will not attach to a target surface and can be killed by a lower dose of microbicide. However, examples of structural scaffolds that inhibit biofilm formation are rare (Musk et al., *Curr. Med. Chem.*, 2006, 13: 2163). The few known examples include the homoserine lactones (Geske et al., *J. Am. Chem. Soc.*, 2005, 127: 12762), which are naturally-occurring bacterial signaling molecules that bacteria use in quorum sensing (Dong et al., *J. Microbiol.*, 2005, 43: 101; Nealson et al., *J. Bacteriol.*, 1970, 104: 313), brominated furanones isolated from the macroalga *Delisea pulchra* (Hentzer et al., *Microbiology-Sgm*, 2002, 148, 87), and ursene triterpenes from the plant *Diospyros dendo* (Hu et al., *J. Nat. Prod.*, 2006, 69, 118).

In addition, bacteria have an unparalleled ability to overcome foreign chemical insult. For example, resistance to vancomycin, "the antibiotic of last resort," has become more prevalent, and strains of vancomycin-resistant *Staphylococcus aureus* have become a serious health risk. It has been predicted that it is simply a matter of time before different bacterial strains develop vancomycin resistance, and the safety net that vancomycin has provided for decades in antibiotic therapy will no longer be available. Therefore, the identification of chemical architectures useful to inhibit biofilm development and/or overcome bacterial antibiotic resistance is needed.

Because of their natural resistance to antibiotics, phagocytic cells, and other biocides, biofilms are difficult, if not impossible, to eradicate. Therefore, the identification of compounds that control biofilms and/or bacterial growth in a variety of settings is of critical need.

SUMMARY OF THE INVENTION

Active compounds useful in the control of biofilms and/or control of bacterial growth are provided herein. In some embodiments, compounds may be provided in the form of a pharmaceutically acceptable salt or prodrug thereof. In some embodiments, compounds may be provided in the form of an agriculturally acceptable salt thereof.

Active compounds include compounds of Formula (I):

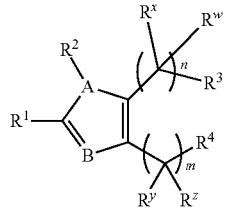

(I)

wherein:
$R^1$, $R^2$, $R^3$ and $R^4$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

each occurrence of $R^w$, $R^x$, $R^y$, and $R^z$ is present or absent (depending upon chain saturation), and is independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

A and B are each independently selected from N, S and O;
n=0 to 20, saturated or unsaturated; and
m=0 to 20, saturated or unsaturated.

Also provided are compounds of Formula (I)(a):

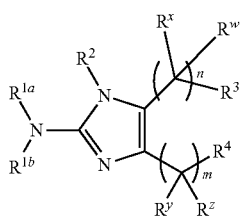

(I)(a)

wherein:
$R^{1a}$, $R^{1b}$, $R^2$, $R^3$ and $R^4$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

each occurrence of $R^w$, $R^x$, $R^y$, and $R^z$ is present or absent (depending upon chain saturation), and is independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

n=0 to 20, saturated or unsaturated; and
m=0 to 20, saturated or unsaturated.

In some embodiments of Formula (I)(a), one of either $R^3$ or $R^4$ is aryl, and the other is H, methyl, or lower alkyl (e.g., C1-C5 alkyl). In some embodiments, n=0 to 5, saturated or unsaturated. In some embodiments, m=0 to 5, saturated or unsaturated.

Also provided are compounds of Formulas (I)(a)(i) and (I)(a)(ii):

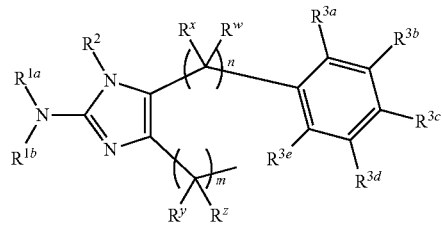

(I)(a)(i)

wherein:
$R^{1a}$, $R^{1b}$, $R^2$, $R^{3a}$, $R^{3b}$, $R^{3c}$, $R^{3d}$, and $R^{3e}$ are each independently selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide;

each occurrence of $R^w$, $R^x$, $R^y$, and $R^z$ is present or absent (depending upon chain saturation), and is independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

n=0 to 20, saturated or unsaturated; and
m=0 to 20, saturated or unsaturated;

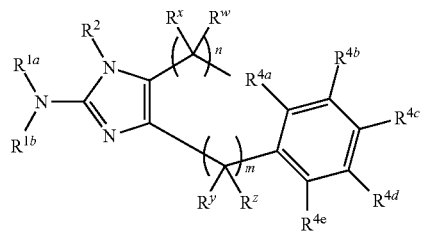

(I)(a)(ii)

wherein:
$R^{1a}$, $R^{1b}$, $R^2$, $R^{4a}$, $R^{4b}$, $R^{4c}$, $R^{4d}$, and $R^{4e}$ are each independently selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide;

each occurrence of $R^w$, $R^x$, $R^y$, and $R^z$ is present or absent (depending upon chain saturation), and is independently selected from the group consisting of: H, hydroxy, acyl, alkyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

n=0 to 20, saturated or unsaturated; and
m=0 to 20, saturated or unsaturated.

In some embodiments of these formulas, $R^{1a}$, $R^{1b}$, $R^2$ are each independently selected from H or alkyl (e.g., lower alkyl having from 1 to 5 carbon atoms).

In some embodiments of these formulas, each occurrence of $R^w$, $R^x$, $R^y$, and $R^z$ is independently selected from H or alkyl (e.g., lower alkyl having from 1 to 5 carbon atoms).

In some embodiments of these formulas, n=0 to 10, or 1 to 9, or 2 to 8, or 3 to 7, or 4 to 6. In some embodiments, n=0, 1, 2, 3, 4, 5, 6, 7, 8, 9, or 10.

In some embodiments of these formulas, m=0 to 10, or 1 to 9, or 2 to 8, or 3 to 7, or 4 to 6. In some embodiments, m=0, 1, 2, 3, 4, 5, 6, 7, 8, 9, or 10.

In some embodiments of these formulas, $R^{3a}$, $R^{3b}$, $R^{3c}$, $R^{3d}$, and $R^{3e}$ are each independently selected from H or alkyl (e.g., lower alkyl having from 1 to 5 carbon atoms). In some embodiments of these formulas, $R^{4a}$, $R^{4b}$, $R^{4c}$, $R^{4d}$, and $R^{4e}$ are each independently selected from H or alkyl (e.g., lower alkyl having from 1 to 5 carbon atoms).

Each of these formulas may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid or peptide.

In some embodiments of the formulas provided herein, the compounds have microbicidal activity (e.g., bactericidal activity, fungicidal activity, etc.).

Biofilm inhibiting and/or microbial growth controlling compositions are provided, which include a carrier and an effective amount of a compound disclosed herein. The carrier may be a pharmaceutically acceptable carrier in some embodiments. The carrier may be an agriculturally acceptable carrier in some embodiments.

Compositions are further provided that include a compound disclosed herein covalently coupled to a substrate. In some embodiments, the substrate includes a polymeric material. In some embodiments, the substrate includes a solid support. In some embodiments, the substrate includes a drainpipe, glaze ceramic, porcelain, glass, metal, wood, chrome, plastic, vinyl, and Formica® brand laminate (The Diller Corporation, Cincinnati, Ohio). In some embodiments, the substrate includes shower curtains or liners, upholstery, laundry, and carpeting.

Biofilm inhibiting and/or microbial growth inhibiting coating compositions are provided, including: (a) a film-forming resin; (b) a solvent that disperses said resin; (c) an effective amount of the compounds or compositions disclosed herein, wherein said effective amount inhibits the growth of a biofilm and/or microorganisms thereon; and (d) optionally, at least one pigment. In some embodiments, the compound is covalently coupled to the resin. In some embodiments, the resin includes a polymeric material.

Substrates coated with coating composition disclosed herein are also provided. In some embodiments, the substrate includes a polymeric material. In some embodiments, the substrate includes a solid support. In some embodiments, the substrate includes a drainpipe, glaze ceramic, porcelain, glass, metal, wood, chrome, plastic, vinyl, and Formica® brand laminate. In some embodiments, the substrate includes shower curtains or liners, upholstery, laundry, and carpeting.

Methods of controlling biofilm formation and/or microbial growth on a substrate are provided, including the step of contacting the substrate with a compound and/or composition disclosed herein in an amount effective to inhibit biofilm formation and/or bacterial growth. In some embodiments, the substrate may include a drainpipe, glaze ceramic, porcelain, glass, metal, wood, chrome, plastic, vinyl, and Formica® brand laminate. In some embodiments, the biofilm includes Gram-positive bacteria.

Methods for treating and/or preventing a bacterial infection in a subject in need thereof are provided, including administering to said subject a compound and/or composition disclosed herein in an amount effective to inhibit a biofilm component or inhibit growth of said bacterial infection.

Also provided are medical devices, including (a) a medical device substrate; and (b) an effective amount of a compound disclosed herein, either coating the substrate, or incorporated into the substrate, wherein said effective amount inhibits the growth of a biofilm and/or bacterial growth thereon. In some embodiments, the medical device substrate may include stents, fasteners, ports, catheters, scaffolds and grafts. In some embodiments, the compound is covalently coupled to said substrate.

Compounds and/or compositions for use in a method to control a biofilm and/or microbial growth are further provided. Also provided is the use of compounds and/or compositions disclosed herein for the preparation of a medicament for the treatment and/or prevention of a bacterial or other microbial infection.

Further provided are methods of preventing, removing or inhibiting microbial biofilm formation or microbial infection in a plant or plant part thereof, comprising applying to the plant or plant part a treatment effective amount of an active compound as described herein, or an agriculturally acceptable salt thereof. In some embodiments, the plant is a fruit or a vegetable crop plant. In some embodiments, the plant is a biomass crop. In some embodiments, the plant is an ornamental plant.

A further aspect of the present invention is an agricultural composition comprising: (a) an agriculturally acceptable carrier (e.g., an aqueous carrier or a solid particulate carrier); and (b) an active compound as described herein, or an agriculturally acceptable salt thereof. In some embodiments, the composition further includes a microbicide. In some embodiments, the microbicide comprises copper (e.g., copper hydroxide). In some embodiments, the microbicide comprises an antibiotic or a bacteriophage. In some embodiments, the composition further includes a plant defense activator. In some embodiments, the composition further includes both a plant defense activator and a microbicide.

Further provided are methods of enhancing the effects of a microbicide (e.g., bactericide, fungicide, etc.) comprising applying an active compound as described herein, in combination with said microbicide. In some embodiments, the microbicide comprises copper (e.g., copper hydroxide). In some embodiments, the microbicide is an antibiotic or a bacteriophage. In some embodiments, the applying step is carried out by applying the active compound and the microbicide simultaneously. In some embodiments, the applying step is carried out by applying the active compound and the microbicide sequentially. In some embodiments, the applying step is carried out by applying to a plant or plant part thereof.

Also provided are methods of enhancing the effects of a plant defense activator comprising applying an active compound as described herein, in combination with said plant defense activator. In some embodiments, the applying step is carried out by applying the active compound and the microbicide simultaneously. In some embodiments, the applying step is carried out by applying the active compound and the microbicide sequentially.

A further aspect of the present invention is an antimicrobial or biofilm preventing, removing or inhibiting compound as described herein, for use in treating or preventing a bacterial or fungal infection in a plant or plant part.

DETAILED DESCRIPTION OF EMBODIMENTS

The present invention is further described below. All patent references referred to in this patent application are hereby incorporated by reference in their entirety as if set forth fully herein.

A. DEFINITIONS

The following definitions are used herein.

"Active compound" as used herein refers to the various embodiments of compounds described in Section B (imidazole derivatives) set forth below.

"Imidazole" refers to the commonly-known structure:

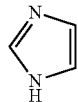

"H" refers to a hydrogen atom. "C" refers to a carbon atom. "N" refers to a nitrogen atom. "O" refers to an oxygen atom. "Halo" refers to F, Cl, Br or I. The term "hydroxy," as used herein, refers to an —OH moiety. "Br" refers to a bromine atom. "Cl" refers to a chlorine atom. "I" refers to an iodine atom. "F" refers to a fluorine atom.

An "acyl group" is intended to mean a group —C(O)—R, where R is a suitable substituent (for example, an acetyl group, a propionyl group, a butyroyl group, a benzoyl group, or an alkylbenzoyl group).

"Alkyl," as used herein, refers to a straight or branched chain hydrocarbon containing from 1 or 2 to 10 or 20 or more carbon atoms (e.g., C2, C3, C4, C5, C6, C7, C8, C9, C10, C11, C12, C13, C14, C15, etc.). In some embodiments the alkyl can be a lower alkyl. "Lower alkyl" refers to straight or branched chain alkyl having from 1 to 3, or from 1 to 5, or from 1 to 8 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like.

As generally understood by those of ordinary skill in the art, "saturation" refers to the state in which all available valence bonds of an atom (e.g., carbon) are attached to other atoms. Similarly, "unsaturation" refers to the state in which not all the available valence bonds are attached to other atoms; in such compounds the extra bonds usually take the form of double or triple bonds (usually with carbon). For example, a carbon chain is "saturated" when there are no double or triple bonds present along the chain or directly connected to the chain (e.g., a carbonyl), and is "unsaturated" when at least one double or triple bond is present along the chain or directly connected to the chain (e.g., a carbonyl). Further, the presence or absence of a substituent depending upon chain saturation will be understood by those of ordinary skill in the art to depend upon the valence requirement of the atom or atoms to which the substituent binds (e.g., carbon).

"Alkenyl," as used herein, refers to a straight or branched chain hydrocarbon containing from 1 or 2 to 10 or 20 or more carbons, and containing at least one carbon-carbon double bond, formed structurally, for example, by the replacement of two hydrogens. Representative examples of "alkenyl" include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl and the like.

"Alkynyl," as used herein, refers to a straight or branched chain hydrocarbon group containing from 1 or 2 to 10 or 20 or more carbon atoms, and containing at least one carbon-carbon triple bond. Representative examples of alkynyl include, but are not limited, to acetylenyl, 1-propynyl, 2-propynyl, 3-butynyl, 2-pentynyl, 1-butynyl and the like.

The term "cycloalkyl," as used herein, refers to a saturated cyclic hydrocarbon group containing from 3 to 8 carbons or more. Representative examples of cycloalkyl include, cyclopropyl, cyclobutyl, cyclopentyl, cyclohexyl, cycloheptyl, and cyclooctyl. In some embodiments, cycloalkyl groups as described herein are optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, etc.

As understood in the art, the term "optionally substituted" indicates that the specified group is either unsubstituted, or substituted by one or more suitable substituents. A "substituent" that is "substituted" is an atom or group which takes the place of a hydrogen atom on the parent chain or cycle of an organic molecule.

"Heterocyclo," as used herein, refers to a monocyclic, bicyclic or tricyclic ring system. Monocyclic heterocycle ring systems are exemplified by any 5 or 6 member ring containing 1, 2, 3, or 4 heteroatoms independently selected from the group consisting of: 0, N, and S. The 5 member ring has from 0 to 2 double bonds, and the 6 member ring has from 0-3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, sulfoxide, thiopyran, triazine, triazole, trithiane, and the like. Bicyclic ring systems are exemplified by any of the above monocyclic ring systems fused to an aryl group as defined herein, a cycloalkyl group as defined herein, or another monocyclic ring system as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, pyranopyridine, quinoline, quinolizine, quinoxaline, quinazoline, tetrahydroisoquinoline, tetrahydroquinoline, thiopyranopyridine, and the like. In some embodiments, heterocyclo groups as described herein are optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, etc.

"Aryl" as used herein refers to a ring system having one or more aromatic rings. Representative examples of aryl include azulenyl, indanyl, indenyl, naphthyl, phenyl, tetrahydronaphthyl, and the like. The aryl groups of this invention can be substituted with 1, 2, 3, 4, or 5 substituents independently selected from alkenyl, alkenyloxy, alkoxy, alkoxyalkoxy, alkoxycarbonyl, alkyl, alkylcarbonyl, alkylcarbonyloxy, alkylsulfinyl, alkylsulfonyl, alkylthio, alkynyl, aryl, aryloxy, azido, arylalkoxy, arylalkyl, aryloxy, carboxy, cyano, formyl, halogen, haloalkyl, haloalkoxy, hydroxy, hydroxyalkyl, mercapto, nitro, sulfamyl, sulfo, sulfonate, —NR'R" (wherein, R' and R" are independently selected from hydrogen, alkyl, alkylcarbonyl, aryl, arylalkyl and formyl), and —C(O)NR'R" (wherein R' and R" are independently selected from hydrogen, alkyl, alkylcarbonyl, aryl, arylalkyl, and formyl).

"Heteroaryl" means a cyclic, aromatic hydrocarbon in which one or more carbon atoms have been replaced with heteroatoms (e.g., N, O or S). If the heteroaryl group contains more than one heteroatom, the heteroatoms may be the same or different. Examples of heteroaryl groups include pyridyl, pyrimidinyl, imidazolyl, thienyl, furyl, pyrazinyl, pyrrolyl, pyranyl, isobenzofuranyl, chromenyl, xanthenyl, indolyl, isoindolyl, indolizinyl, triazolyl, pyridazinyl, indazolyl, purinyl, quinolizinyl, isoquinolyl, quinolyl, phthalazinyl, naphthyridinyl, quinoxalinyl, isothiazolyl, and benzo[b]thienyl. Preferred heteroaryl groups are five and six membered rings and contain from one to three heteroatoms independently selected from the group consisting of: O, N, and S. The heteroaryl group, including each heteroatom, can be unsubstituted or substituted with from 1 to 4 suitable substituents, as chemically feasible. For example, the heteroatom S may be substituted with one or two oxo groups, which may be shown as =O.

"Alkoxy," as used herein, refers to an alkyl group, as defined herein, appended to the parent molecular moiety through an oxy group, as defined herein. Representative examples of alkoxy include, but are not limited to, methoxy, ethoxy, propoxy, 2-propoxy, butoxy, tert-butoxy, pentyloxy, hexyloxy and the like.

An "amine" or "amino" is intended to mean the group —NH$_2$.

An "amide" as used herein refers to an organic functional group having a carbonyl group (C=O) linked to a nitrogen atom (N), or a compound that contains this group, generally depicted as:

wherein, R and R' can independently be any covalently-linked atom or atoms.

A "thiol" or "mercapto" refers to an —SH group or to its tautomer =S.

A "sulfone" as used herein refers to a sulfonyl functional group, generally depicted as:

wherein, R can be any covalently-linked atom or atoms.

A "sulfoxide" as used herein refers to a sulfinyl functional group, generally depicted as:

wherein, R can be any covalently-linked atom or atoms.

The term "oxo," as used herein, refers to a =O moiety.
The term "oxy," as used herein, refers to a —O— moiety.
"Nitro" refers to the organic compound functional group —NO$_2$.

"Carbonyl" is a functional group having a carbon atom double-bonded to an oxygen atom (—C=O). "Carboxy" as used herein refers to a —COOH functional group, also written as —CO$_2$H or —(C=O)—OH.

"Amino acid sidechain" as used herein refers to any of the 20 commonly known groups associated with naturally-occurring amino acids, or any natural or synthetic homologue thereof. An "amino acid" includes the sidechain group and the amino group, alpha-carbon atom, and carboxy groups, as commonly described in the art. Examples of amino acids include glycine, and glycine that is substituted with a suitable substituent as described herein, such as alkyl, alkenyl, alkynyl, cycloalkyl, heterocyclo, aryl, heteroaryl, alkoxy, carbonyl, carboxy, etc., or a agriculturally acceptable salt thereof. For example, "Histidine" is one of the 20 most commonly known amino acids found naturally in proteins. It contains an imidazole side chain substituent. Other examples of naturally-occurring amino acids include lysine, arginine, aspartic acid, glutamic acid, asparagine, glutamine, serine, threonine, tyrosine, alanine, valine, leucine, isoleucine, phenylalanine, methionine, cryptophan, and cysteine. Also included in the definitions of "amino acid sidechain" and "amino acid" is proline, which is commonly included in the definition of an amino acid, but is technically an imino acid. As used in this application, both the naturally-occurring L-, and the non-natural D-amino acid enantiomers are included. The single letter code for amino acids is A (Ala), C (Cys), D (Asp), E (Glu), F (Phe), G (Gly), H (His), I (Ile), K (Lys), L (Leu), M (Met), N (Asn), P (Pro), Q (Gln), R (Arg), S (Ser), T (Thr), V (Val), W (Trp), and Y (Tyr). A "peptide" is a linear chain of amino acids covalently linked together, typically through an amide linkage, and contains from 1 or 2 to 10 or 20 or more amino acids, and is also optionally substituted and/or branched.

A "pharmaceutically acceptable salt" is intended to mean a salt that retains the biological effectiveness of the free acids and bases of a specified compound and that is not biologically or otherwise undesirable. Examples of pharmaceutically acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycollates, tartrates, methane-sulfonates, propanesulfonates, naphthalene-1-sulfonates, naphthalene-2-sulfonates, and mandelates.

A "prodrug" is intended to mean a compound that is converted under physiological conditions or by solvolysis or metabolically to a specified compound that is pharmaceutically active. A thorough discussion is provided in T. Higuchi and V. Stella, Prodrugs as Novel delivery Systems, Vol. 14 of the A.C.S. Symposium Series and in Edward B. Roche, ed., Bioreversible Carriers in Drug Design, American Pharmaceutical Association and Pergamon Press, 1987, both of which are incorporated by reference herein in their entireties.

"Plant" as used herein includes all members of the plant kingdom, including higher (or "vascular") plants and lower ("non-vascular") plants, and particularly including all plants in the divisions Filicinae, Gymnospermae (or "gymnosperm"), and Angiospermae (or "Angiosperm"). Nonvascular plants of the present invention include, but are not limited to, bryophytes.

A plant of the present invention includes, but is not limited to, a crop plant, a turf grass, an ornamental species, a species grown for timber or pulp, a species grown for biofuels, and a species grown for pharmaceuticals. Additionally, plants of the present invention include, but are not limited to, tobacco, tomato, potato, sugar beet, pea, carrot, cauliflower, broccoli, soybean, canola, sunflower, alfalfa, cotton, rapeseed, *Arabidopsis*, peach, pepper, apple, chile, peanut, orange, grape, coffee, cassava, spinach, lettuce, cucumber, wheat, maize, rye, rice, turfgrass, oat, barley, sorghum, millet, sugarcane, or banana.

"Plant part" as used herein refers to seeds, roots, leaves, shoots, fruits (e.g., apples, pineapples, citrus fruit, etc.), vegetables, tubers, flowers (e.g., cut flowers such as roses, as well as the reproductive parts of plants), petals, stem, trunk, etc., harvested or collected from a plant as described herein. The plant part of a vascular plant may be a non-vascular part, such as a seed or meristem (growing tip of a shoot).

"Applying" as described herein can be carried out directly or indirectly by any suitable technique, including topically applying to the plant or plant part, applying to the media in which the plant or plant part is grown, stored, displayed or maintained (e.g., adding to water in which the stems of cut flowers are placed), etc. Note that the plant may be grown in any suitable media, including but not limited to soil, potting soil, soilless media such as sand and hydroponic media (including solution culture, medium culture, and deep water culture), etc.

"Agricultural composition" as described herein may be in any suitable form, including but not limited to: wettable powders, dry flowables, soluble powders, water dispersibles, liquids, dusts, emulsifiable concentrates, flowables, fumigants, water dispersable granules, liquid concentrates, granules, water soluble packages, wettable powders in water soluble films, emulsions, etc.

B. ACTIVE COMPOUNDS

Active compounds are provided below. In some of the embodiments provided, active compounds are imidazole derivatives. Active compounds as described herein can be prepared as detailed below or in accordance with known procedures or variations thereof that will be apparent to those skilled in the art. Compounds may be provided in the form of a salt, such as a pharmaceutically acceptable salt, or a prodrug, or an agriculturally acceptable salt thereof, as appropriate.

As will be appreciated by those of skill in the art, the active compounds of the various formulas disclosed herein may contain chiral centers, e.g. asymmetric carbon atoms. Thus, the present invention is concerned with the synthesis of both: (i) racemic mixtures of the active compounds, and (ii) enantiomeric forms of the active compounds. The resolution of racemates into enantiomeric forms can be done in accordance with known procedures in the art. For example, the racemate may be converted with an optically active reagent into a diastereomeric pair, and the diastereomeric pair subsequently separated into the enantiomeric forms.

Geometric isomers of double bonds and the like may also be present in the compounds disclosed herein, and all such stable isomers are included within the present invention unless otherwise specified. Also included in active compounds of the invention are tautomers (e.g., tautomers of imidazole) and rotamers. All chains defined by the formulas herein which include three or more carbons may be saturated or unsaturated unless otherwise indicated.

Active compounds include compounds of Formula (I):

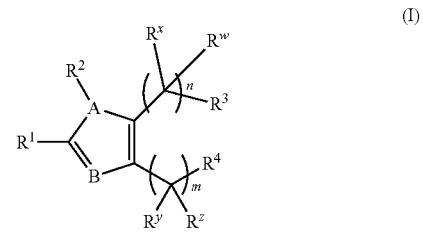

wherein:

$R^1$, $R^2$, $R^3$ and $R^4$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

each occurrence of $R^w$, $R^x$, $R^y$, and $R^z$ is present or absent (depending upon chain saturation), and is independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide; and A and B are each independently selected from N, S and O;

n=0 to 20, saturated or unsaturated; and m=0 to 20, saturated or unsaturated.

In some embodiments of Formula (I), $R^1$ is a substituted amino, and A and B are each N, generally depicted by Formula (I)(a):

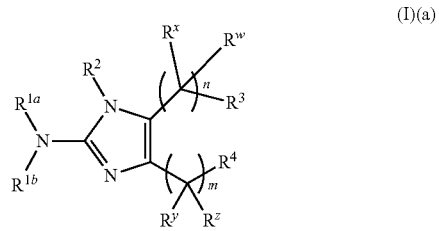

wherein:

$R^{1a}$, $R^{1b}$, $R^2$, $R^3$ and $R^4$ are each independently selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide;

each occurrence of $R^w$, $R^x$, $R^y$, and $R^z$ is present or absent (depending upon chain saturation), and is independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

n=0 to 20, saturated or unsaturated; and m=0 to 20, saturated or unsaturated.

In some embodiments of Formula (I)(a), one of either $R^3$ or $R^4$ is aryl, and the other is methyl.

In some embodiments of Formula (I)(a), one of either $R^3$ or $R^4$ is phenyl, and the other is methyl, generally depicted by Formulas (I)(a)(i) and (I)(a)(ii):

(I)(a)(i)

wherein:

$R^{1a}$, $R^{1b}$, $R^2$, $R^{3a}$, $R^{3b}$, $R^{3c}$, $R^{3d}$, and $R^{3e}$ are each independently selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide;

each occurrence of $R^w$, $R^x$, $R^y$, and $R^z$ is present or absent (depending upon chain saturation), and is independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

n=0 to 20, saturated or unsaturated; and m=0 to 20, saturated or unsaturated;

(I)(a)(ii)

wherein:

$R^{1a}$, $R^{1b}$, $R^2$, $R^{4a}$, $R^{4b}$, $R^{4c}$, $R^{4d}$, and $R^{4e}$ are each independently selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide;

each occurrence of $R^w$, $R^x$, $R^y$, and $R^z$ is present or absent (depending upon chain saturation), and is independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

n=0 to 20; and m=0 to 20.

In some embodiments of these formulas, $R^{1a}$, $R^{1b}$, $R^2$ are each independently selected from H or alkyl (e.g., lower alkyl having from 1 to 5 carbon atoms).

In some embodiments of these formulas, each occurrence of $R^w$, $R^x$, $R^y$, and $R^z$ is independently selected from H or alkyl (e.g., lower alkyl having from 1 to 5 carbon atoms).

In some embodiments of these formulas, n=0 to 10, or 1 to 9, or 2 to 8, or 3 to 7, or 4 to 6. In some embodiments, n=0, 1, 2, 3, 4, 5, 6, 7, 8, 9, or 10.

In some embodiments of these formulas, m=0 to 10, or 1 to 9, or 2 to 8, or 3 to 7, or 4 to 6. In some embodiments, m=0, 1, 2, 3, 4, 5, 6, 7, 8, 9, or 10.

In some embodiments of these formulas, $R^{3a}$, $R^{3b}$, $R^{3c}$, $R^{3d}$, and $R^{3e}$ are each independently selected from H or alkyl (e.g., lower alkyl having from 1 to 5 carbon atoms). In some embodiments of these formulas, $R^{4a}$, $R^{4b}$, $R^{4c}$, $R^{4d}$, and $R^{4e}$ are each independently selected from H or alkyl (e.g., lower alkyl having from 1 to 5 carbon atoms).

Each of these formulas may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

C. COMPOSITIONS

In some embodiments, biofilm and/or bacterial growth inhibiting compositions are provided, comprising a carrier and an effective amount of active compound. "Biofilm" or "biofilms" refer to communities of microorganisms that are attached to a substrate. The microorganisms often excrete a protective and adhesive matrix of polymeric compounds. They often have structural heterogeneity, genetic diversity, and complex community interactions. "Biofilm inhibiting", "biofilm reducing", "biofilm resistant", "biofilm controlling" or "antifouling" refer to inhibition of the establishment or growth of a biofilm, or decrease in the amount of organisms that attach and/or grow upon a substrate. As used herein, a "substrate" can include any living or nonliving structure. For example, biofilms often grow on synthetic materials submerged in an aqueous solution or exposed to humid air, but they also can form as floating mats on a liquid surface, in which case the microorganisms are adhering to each other or to the adhesive matrix characteristic of a biofilm.

"Bacterial growth" inhibiting, reducing or controlling refers to inhibition of the growth and/or reduction in the number of bacteria, whether in a biofilm or planktonic. Thus, in some embodiments, active compounds are bactericidal and/or bacteriostatic to planktonic bacteria.

In some embodiments, active compounds have the ability to kill or to inhibit the growth of a broad range of microorganisms (e.g., bacteria, fungal cells, protozoa, etc.), whether as a disinfectant, an antiseptic, or an antibiotic. "Microbial growth" inhibiting, reducing or controlling refers to inhibition of the growth and/or reduction in the number of microorganisms, in general. Thus, in some embodiments, active compounds are biocidal and/or biostatic to bacteria, fungal cells, protozoa, etc.

An "effective amount" of a biofilm inhibiting or bacterial growth inhibiting composition is that amount which is necessary to carry out the composition's function of inhibiting a biofilm, inhibiting bacterial growth, and/or inhibiting growth of microorganisms.

In some embodiments, the carrier is a pharmaceutically acceptable carrier. A "pharmaceutically acceptable carrier" as used herein refers to a carrier that, when combined with an active compound of the present invention, facilitates the application or administration of that active compound for its intended purpose to prevent or inhibit biofilm formation, remove an existing biofilm, and/or inhibit bacterial or microbial growth. The active compounds may be formulated for administration in a pharmaceutically acceptable carrier in accordance with known techniques. See, e.g., Remington, *The Science and Practice of Pharmacy* ($9^{th}$ Ed. 1995). The pharmaceutically acceptable carrier must, of course, also be acceptable in the sense of being compatible with any other ingredients in the composition. The carrier may be a solid or a liquid, or both, and is preferably formulated with the compound as a unit-dose composition, for example, a tablet, which may contain from 0.01 or 0.5% to 95% or 99% by weight of the active compound. One or more active compounds may be included in the compositions of the invention, which may be prepared by any of the well-known techniques of pharmacy comprising admixing the components, optionally including one or more accessory ingredients.

In general, compositions may be prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

The compositions of the invention include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular active compound that is being used. Routes of parenteral administration include intrathecal injection and intraventricular injection into a ventricle of the brain.

Compositions suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such compositions may be prepared by any suitable method of pharmacy, which includes the step of bringing into association the active compound and a suitable carrier (which may contain one or more accessory ingredients as noted above).

Compositions suitable for buccal (sub-lingual) administration include lozenges comprising the active compound in a flavored base, usually sucrose and acacia or tragacanth; and pastilles comprising the compound in an inert base such as gelatin and glycerin or sucrose and acacia.

Compositions of the present invention suitable for parenteral administration comprise sterile aqueous and non-aqueous injection solutions of the active compound, which preparations are preferably isotonic with the blood of the intended recipient. These preparations may contain antioxidants, buffers, bacteriostats and solutes that render the composition isotonic with the blood of the intended recipient. Aqueous and non-aqueous sterile suspensions may include suspending agents and thickening agents. The compositions may be presented in unit/dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described.

For example, in one aspect of the present invention, there is provided an injectable, stable, sterile composition comprising an active compound as described herein, or a salt or prodrug thereof, in a unit dosage form in a sealed container. The compound or salt is provided in the form of a lyophilizate that is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent that is physiologically acceptable may be employed in sufficient quantity to emulsify the compound or salt in an aqueous carrier. One such useful emulsifying agent is phosphatidyl choline.

Compositions suitable for rectal administration are preferably presented as unit dose suppositories. These may be prepared by mixing the active compound with one or more conventional solid carriers, for example, cocoa butter, and then shaping the resulting mixture.

Compositions suitable for topical application to the skin preferably take the form of an ointment, cream, lotion, paste, gel, spray, aerosol, or oil. Carriers that may be used include petroleum jelly, lanoline, polyethylene glycols, alcohols (e.g., ethanol, isopropanol, etc.), transdermal enhancers, and combinations of two or more thereof.

Compositions suitable for transdermal administration may be presented as discrete patches adapted to remain in intimate contact with the epidermis of the recipient for a prolonged period of time. Compositions suitable for transdermal administration may also be delivered by iontophoresis (see, for example, *Pharmaceutical Research* 3 (6):318 (1986)) and typically take the form of an optionally buffered aqueous solution of the active compound.

Also provided in some embodiments are compositions comprising an active compound and a biocide. A "biocide" or "microbicide" as used herein refers to a substance with the ability to kill or to inhibit the growth of microorganisms (e.g., bacteria, fungal cells, protozoa, etc.), whether as a disinfectant, an antiseptic, or an antibiotic, which substance is not an active compound give above in Section B. Similarly, "microbicidal activity" refers to the killing or growth inhibition of microorganisms. Common biocides include oxidizing and non-oxidizing chemicals. Examples of oxidizing biocides include chlorine, chlorine dioxide, and ozone. Examples of non-oxidizing biocides include quaternary ammonium compounds, formaldehyde, and anionic and non-anionic surface agents. Chlorine is the most common biocide used in sanitizing water systems. Chlorhexidine (e.g., chlorhexidine gluconate) is a biocide commonly used as an antiseptic in oral rinses and skin cleansers. Iodine preparations are also commonly used as disinfectants.

An "antibiotic" as used herein is a type of "biocide." Common antibiotics include aminoglycosides, carbacephems (e.g., loracarbef), carbapenems, cephalosporins, glycopeptides (e.g., teicoplanin and vancomycin), macrolides, monobactams (e.g., aztreonam) penicillins, polypeptides (e.g., bacitracin, colistin, polymyxin B), quinolones, sulfonamides, tetracyclines, etc. Antibiotics treat infections by either killing or preventing the growth of microorganisms. Many act to inhibit cell wall synthesis or other vital protein synthesis of the microorganisms.

Aminoglycosides are commonly used to treat infections caused by Gram-negative bacteria such as *Escherichia coli* and *Klebsiella*, particularly *Pseudomonas aeroginosa*. Examples of aminoglycosides include, but are not limited to amikacin, gentamicin, kanamycin, neomycin, netilmicin, streptomycin, tobramycin, and paromomycin.

Carbapenems are broad-specrum antibiotics, and include, but are not limited to, ertapenem, doripenem, imipenem/cilstatin, and meropenem.

Cephalosporins include, but are not limited to, cefadroxil, cefazolin, cefalotin (cefalothin), cefalexin, cefaclor, cefamandole, cefoxitin, cefprozil, loracarbef, cefuroxime, cefixime, cefdinir, cefditoren, cefoperazone, cefotaxime, cefpodoxime, ceftazidime, ceftibuten, ceftizoxime, ceftriaxone, cefepime, cefpirome, and ceftobiprole.

Macrolides include, but are not limited to, azithromycin, clarithromycin, dirithromycin, erythromycin, roxithromycin, troleandomycin, telithromycin and spectinomycin.

Penicillins include, but are not limited to, amoxicillin, ampicillin, azlocillin, bacampicillin, carbenicillin, cloxacillin, dicloxacillin, flucloxacillin, mezlocillin, meticillin, nafcillin, oxacillin, penicillin, piperacillin and ticarcillin.

Quinolones include, but are not limited to, ciprofloxacin, enoxacin, gatifloxacin, gemifloxacin, levofloxacin, lomefloxacin, moxifloxacin, norfloxacin, ofloxacin and trovafloxacin.

Sulfonamides include, but are not limited to, mafenide, prontosil, sulfacetamide, sulfamethizole, sulfanilamide, sulfasalazine, sulfisoxazole, trimethoprim, and co-trimoxazole (trimethoprim-sulfamethoxazole).

Tetracyclines include, but are not limited to, demeclocycline, doxycycline, minocycline, oxytetracycline and tetracycline.

Other antibiotics include arsphenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinupristin/dalfopristin, rifampin (rifampicin), tinidazole, etc.

In some embodiments, a dentifrice composition is provided comprising the active compounds. A "dentifrice" is a substance that is used to clean the teeth. It may be in the form of, e.g., a paste or powder. Commonly known dentifrices include toothpaste, mouthwash, chewing gum, dental floss, and dental cream. Other examples of dentifrices include toothpowder, mouth detergent, troches, dental or gingival massage cream, dental strips, dental gels, and gargle tablets. Examples of dentifrice compositions comprising toothpaste and mouthwash are found in U.S. Pat. No. 6,861,048 (Yu et al.); U.S. Pat. No. 6,231,836 (Takhtalian et al.); and U.S. Pat. No. 6,331,291 (Glace et al.); each incorporated by reference herein in their entirety.

A coating composition is also provided. A "coating" as used herein is generally known. Any of a variety of organic and aqueous coating compositions, with or without pigments, may be modified to contain biofilm inhibiting compositions as described herein, including but not limited to those described in U.S. Pat. Nos. 7,109,262, 6,964,989, 6,835,459, 6,677,035, 6,528,580, 6,235,812, etc., each incorporated by reference herein in their entirety.

In general, the coatings comprise a film-forming resin, an aqueous or organic solvent that disperses the resin; and, optionally, at least one pigment. Other ingredients such as colorants, secondary pigments, stabilizers and the like can be included if desired. However, for use in the present invention the compositions further comprise one or more biofilm inhibiting compounds as described herein, which may be carried by or dispersed in the solvent and/or resin, so that the biofilm inhibiting compounds are dispersed or distributed on the substrate an article coated. A resin may carry the biofilm inhibiting compounds through covalent attachment through means well known in the art. The resin may comprise, for example, a polymeric material. A polymeric material is a material that is comprised of large molecules made from associated smaller repeating structural units, often covalently linked. Common examples of polymeric materials are unsaturated polyester resins, and epoxy resins.

Any suitable article can be coated, in whole or in part, with a composition of the invention. Suitable articles include, but are not limited to, automobiles and airplanes (including substrates such as wing and propeller surfaces for aerodynamic testing), boat vessel hulls (including interior and exterior surfaces thereof), pressure vessels (including interior and exterior surfaces thereof) medical implants, windmills, etc. Coating of the article with the composition can be carried out by any suitable means, such as by brushing, spraying, electrostatic deposition, dip coating, doctor blading, etc.

Common biocides used for microbial control in plants include copper compounds. Examples of copper compounds include, but are not limited to, Bordeaux mixture, copper hydroxide, copper oxychloride, copper sulfate, cuprous oxide, mancopper or oxine-copper. However, microorganisms (e.g., bacteria such as *Xanthomonas* and *Pseudomonas*) may become resistant to treatment with copper. In some embodiments, resistant microorganisms (e.g., copper-resistant bacteria) are rendered more susceptible to a microbicides and/or the effectiveness of treatment with a microbicides is enhanced upon application in combination with an active compound described herein (e.g., fruit or vegetable yield is increased as compared to diseased plant producing the fruit or vegetable that is untreated or treated only with the microbicide).

Other biocides useful for microbial control in plants include, but are not limited to, azoles such as azaconazole, bitertanol, propiconazole, difenoconazole, diniconazole, cyproconazole, epoxiconazole, fluquinconazole, flusilazole, flutriafol, hexaconazole, imazalil, imibenconazole, ipconazole, tebuconazole, tetraconazole, fenbuconazole, metconazole, myclobutanil, perfurazoate, penconazole, bromuconazole, pyrifenox, prochloraz, triadimefon, triadimenol, triflumizole or triticonazole; pyrimidinyl carbinoles such as ancymidol, fenarimol or nuarimol; 2-amino-pyrimidine such as bupirimate, dimethirimol or ethirimol; morpholines such as dodemorph, fenpropidin, fenpropimorph, spiroxamin or tridemorph; anilinopyrimidines such as cyprodinil, pyrimethanil or mepanipyrim; pyrroles such as fenpiclonil or fludioxonil; phenylamides such as benalaxyl, furalaxyl, metalaxyl, R-metalaxyl, ofurace or oxadixyl; benzimidazoles such as benomyl, carbendazim, debacarb, fuberidazole or thiabendazole; dicarboximides such as chlozolinate, dichlozoline, iprodine, myclozoline, procymidone or vinclozolin; carboxamides such as carboxin, fenfuram, flutolanil, mepronil, oxycarboxin or thifluzamide; guanidines such as guazatine, dodine or iminoctadine; strobilurines such as azoxystrobin, kresoxim-methyl, metominostrobin, SSF-129, methyl 2[(2-trifluoromethyl)-pyrid-6-yloxymethyl]-3-methoxy-acrylate or 2-[{α[(α-methyl-3-trifluoromethyl-benzyl)imino]-oxy}-o-tolyl]-glyoxylic acid-methylester-O-methyloxime (trifloxystrobin); dithiocarbamates such as ferbam, mancozeb, maneb, metiram, propineb, thiram, zineb or ziram; N-halomethylthio-dicarboximides such as captafol, captan, dichlofluanid, fluoromide, folpet or tolyfluanid; nitrophenol derivatives such as dinocap or nitrothal-isopropyl; organo phosphorous derivatives such as edifenphos, iprobenphos, isoprothiolane, phosdiphen, pyrazophos or toclofos-methyl; and other compounds of diverse structures such as acibenzolar-S-methyl, harpin, anilazine, blasticidin-S, chinomethionat, chloroneb, chlorothalonil, cymoxanil, dichione, diclomezine, dicloran, diethofencarb, dimethomorph, dithianon, etridiazole, famoxadone, fenamidone, fentin, ferimzone, fluazinam, flusulfamide, fenhexamid, fosetyl-aluminium, hymexazol, kasugamycin, methasulfocarb, pencycuron, phthalide, polyoxins, probenazole, propamocarb, pyroquilon, quinoxyfen, quintozene, sulfur, triazoxide, tricyclazole, triforine, validamycin, (S)-5-methyl-2-methylthio-5-phenyl-3-phenylamino-3,5-di-hydroimidazol-4-one (RPA 407213), 3,5-dichloro-N-(3-chloro-1-ethyl-1-methyl-2-oxopropyl)-4-methylbenzamide (RH-7281), N-allyl-4,5-dimethyl-2-trimethylsilylthiophene-3-carboxamide (MON 65500), 4-chloro-4-cyano-N,N-dimethyl-5-p-tolylimidazole-1-sulfon-amide (IKF-916), N-(1-cyano-1,2-dimethylpropyl)-2-(2,4-dichlorophenoxy)-propionamide (AC 382042) or iprovalicarb (SZX 722).

Other microbicides that may be used in combination with the active compounds of the present invention include bacteriophages (bacterial viruses) such as *Bacillus*. Examples of bacteriophage microbicides include, but are not limited to, AgriPhage™ (OmniLytics, Inc., Salt Lake City, Utah) and Serenade® (AgraQuest, Davis, Calif.). See, e.g., U.S. Pat. Nos. 5,919,447 and 6,077,506 to Marrone et al.; U.S. Pat. No. 6,103,228 to Heins et al.; and U.S. Patent Application Publication 20080152684.

In some embodiments, an active compound described herein is applied in combination with a plant defense activator. A "plant defense activator" as used herein is a compound that improves disease resistance by activating a plant's natural defense mechanisms, e.g., induces the plant to produce disease-fighting compounds. Examples of plant defense activators include, but are not limited to, prohexadione-calcium (Apogee), Cropset (plant booster element complex), probenazole, potassium phosphate (e.g., ProPhyt®, Helena Chemical Company), harpin protein (e.g., Messenger®, Eden Biosciences Ltd, Bothell, Wash.), acibenzolar or acibenzolar-S-methyl (e.g., Actigard™, Syngenta Crop Production, Inc, Greensboro, N.C.), streptomycin sulfate, *reynoutria sachalinensis* extract (reysa), etc.

Active compounds can be used to prepare agrochemical compositions in like manner as other antimicrobial compounds. See, e.g., U.S. Pat. Application 2006/0094739; see also U.S. Pat. Nos. 6,617,330; 6,616,952; 6,569,875; 6,541,500, and 6,506,794.

Active compounds described herein can be used for protecting plants against diseases that are caused by microorganisms, including biofilm-forming microorganisms. The active compounds can be used in the agricultural sector and related fields as active ingredients for controlling plant pests. The active compounds can be used to inhibit or destroy the pests that occur on plants or parts of plants (fruit, blossoms, leaves, stems, tubers, roots) of different crops of useful plants, optionally while at the same time protecting also those parts of the plants that grow later e.g. from phytopathogenic microorganisms.

Active compounds may be used as dressing agents for the treatment of plant propagation material, in particular of seeds (e.g., fruit, tubers, grains) and plant cuttings (e.g., rice), for the protection against fungal infections as well as against phytopathogenic fungi occurring in the soil.

The active compounds can be used in the form of compositions and can be applied to the crop area or plant to be treated, simultaneously or in succession with further compounds. These further compounds can be, for example, fertilizers or micronutrient donors or other preparations which influence the growth of plants. They can also be selective herbicides as well as insecticides, fungicides, bactericides, nematicides, molluscicides, plant growth regulators, plant activators or mixtures of several of these preparations, if desired together with further carriers, surfactants or application promoting adjuvants customarily employed in the art of formulation.

Suitable carriers and adjuvants can be solid or liquid and are substances useful in formulation technology, e.g., natural or regenerated mineral substances, solvents, dispersants, wetting agents, tackifiers, thickeners, binders or fertilizers.

The active compounds are used in unmodified form or, preferably, together with the adjuvants conventionally employed in the art of formulation. To this end they are conveniently formulated in known manner to emulsifiable concentrates, coatable pastes, directly sprayable or dilutable solutions, dilute emulsions, wettable powders, soluble powders, dusts, granulates, and also encapsulations e.g., in polymeric substances. As with the type of the compositions, the methods of application, such as spraying, atomizing, dusting, scattering, coating or pouring, are chosen in accordance with the intended objectives and the prevailing circumstances.

The formulation, i.e., the compositions containing the active compound and, if desired, a solid or liquid adjuvant, are prepared in known manner, typically by intimately mixing and/or grinding the compound with extenders, e.g., solvents, solid carriers and, optionally, surface active compounds (surfactants). Suitable carriers and adjuvants may be solid or liquid and correspond to the substances ordinarily employed in formulation technology, such as, e.g. natural or regenerated mineral substances, solvents, dispersants, wetting agents, tackifiers, thickeners, binding agents or fertilizers. Such carriers are, for example, described in WO 97/33890. Further surfactants customarily employed in the art of formulation are known to the expert or can be found in the relevant literature.

The agrochemical formulations will usually contain from 0.1 to 99% by weight, preferably from 0.1 to 95% by weight, of a compound described herein, 99.9 to 1% by weight, preferably 99.8 to 5% by weight, of a solid or liquid adjuvant, and from 0 to 25% by weight, preferably from 0.1 to 25% by weight, of a surfactant. Whereas it is preferred to formulate commercial products as concentrates, the end user will normally use dilute formulations.

The compositions may also contain further adjuvants such as stabilizers, antifoams, viscosity regulators, binders or tackifiers as well as fertilizers, micronutrient donors or other formulations for obtaining special effects.

D. METHODS OF USE

Methods of controlling biofilm formation and/or bacterial growth on a substrate are disclosed, comprising the step of administering an active compound to a substrate in an amount effective to inhibit biofilm formation and/or bacterial growth. A "substrate" as used herein is a base on which an organism, such as those commonly found in biofilms, may live. The term "substrate," as used herein, refers to any substrate, whether in an industrial, medical, or agricultural setting, that provides or can provide an interface between an object and a fluid, permitting at least intermittent contact between the object and the fluid. A substrate, as understood herein, further provides a plane whose mechanical structure, without further treatment, is compatible with the adherence of microorganisms. Substrates compatible with biofilm formation may be natural or synthetic, and may be smooth or irregular. Fluids contacting the substrates can be stagnant or flowing, and can flow intermittently or continuously, with laminar or turbulent or mixed flows. A substrate upon which a biofilm forms can be dry at times with sporadic fluid contact, or can have any degree of fluid exposure including total immersion. Fluid contact with the substrate can take place via aerosols or other means for air-borne fluid transmission.

Biofilm formation with health implications can involve those substrates in all health-related environments, including substrates found in medical environments and those substrates in industrial or residential environments that are involved in those functions essential to human well being, for example, nutrition, sanitation and the prevention of disease. Substrates found in medical environments include the inner and outer aspects of various instruments and devices, whether disposable or intended for repeated uses. Examples include the entire spectrum of articles adapted for medical use, including scalpels, needles, scissors and other devices used in invasive surgical, therapeutic or diagnostic procedures; implantable medical devices, including artificial blood vessels, catheters and other devices for the removal or delivery of fluids to patients, artificial hearts, artificial kidneys, orthopedic pins, plates and implants; catheters and other tubes (including urological and biliary tubes, endotracheal tubes, peripherably insertable central venous catheters, dialysis catheters, long term tunneled central venous catheters, peripheral venous catheters, short term central venous catheters, arterial catheters, pulmonary catheters, Swan-Ganz catheters, urinary catheters, peritoneal catheters), urinary devices (including long term urinary devices, tissue bonding urinary devices, artificial urinary sphincters, urinary dilators), shunts (including ventricular or arterio-venous shunts); prostheses (including breast implants, penile prostheses, vascular grafting prostheses, heart valves, artificial joints, artificial larynxes, otological implants), vascular catheter ports, wound drain tubes, hydrocephalus shunts, pacemakers and implantable defibrillators, and the like. Other examples will be readily apparent to practitioners in these arts. Substrates found in the medical environment also include the inner and outer aspects of pieces of medical equipment, medical gear worn or carried by personnel in the health care setting. Such substrates can include counter tops and fixtures in areas used for medical procedures or for preparing medical apparatus, tubes and canisters used in respiratory treatments, including the administration of oxygen, of solubilized drugs in nebulizers and of anesthetic agents. Also included are those substrates intended as biological barriers to infectious organisms in medical settings, such as gloves, aprons and faceshields. Commonly used materials for biological barriers may be latex-based or non-latex based. Vinyl is commonly used as a material for non-latex surgical gloves. Other such substrates can include handles and cables for medical or dental equipment not intended to be sterile. Additionally, such substrates can include those non-sterile external substrates of tubes and other apparatus found in areas where blood or body fluids or other hazardous biomaterials are commonly encountered.

Substrates in contact with liquids are particularly prone to biofilm formation. As an example, those reservoirs and tubes used for delivering humidified oxygen to patients can bear biofilms inhabited by infectious agents. Dental unit waterlines similarly can bear biofilms on their substrates, providing a reservoir for continuing contamination of the system of flowing an aerosolized water used in dentistry. Sprays, aerosols and nebulizers are highly effective in disseminating biofilm fragments to a potential host or to another environmental site. It is especially important to health to prevent biofilm formation on those substrates from where biofilm fragments can be carried away by sprays, aerosols or nebulizers contacting the substrate.

Other substrates related to health include the inner and outer aspects of those articles involved in water purification, water storage and water delivery, and articles involved in food processing. Substrates related to health can also include the inner and outer aspects of those household articles involved in providing for nutrition, sanitation or disease prevention. Examples can include food processing equipment for home use, materials for infant care, tampons and toilet bowls. "Substrate" as used herein also refers to a living substrate, such as the inner ear of a patient.

Substrates can be smooth or porous, soft or hard. Substrates can include a drainpipe, glaze ceramic, porcelain, glass, metal, wood, chrome, plastic, vinyl, Formica® brand laminate, or any other material that may regularly come in contact with an aqueous solution in which biofilms may form and grow. The substrate can be a substrate commonly found on household items such as shower curtains or liners, upholstery, laundry, and carpeting.

A substrate on which biofilm inhibiting is important is that of a ship hull. Biofilms, such as those of *Halomonas pacifica*, promote the corrosion of the hull of ships and also increase the roughness of the hull, increasing the drag on the ship and thereby increasing fuel costs. The biofilm can also promote the attachment of larger living structures such as barnacles on the ship hull. Fuel can account for half of the cost of marine shipping, and the loss in fuel efficiency due to biofilm formation is substantial.

Substrates on which biofilms can adhere include those of living organisms, as in the case of humans with chronic infections caused by biofilms, as discussed above. Biofilms can also form on the substrates of food contact surfaces, such as those used for processing seafood, and also on food products themselves. Examples of seafood products that may have biofilm contamination include oysters. Human infections caused by the ingestion of raw oysters has been linked to *Vibrio vulnificus* bacterium. *Vibrio* bacteria attach to algae and plankton in the water and transfer to the oysters and fish that feed on these organisms.

Other examples of substrates or devices on which biofilms can adhere can be found in U.S. Pat. Nos. 5,814,668 and 7,087,661; and U.S. Pat. Appln. Publication Nos. 2006/0228384 and 2006/0018945, each of which is incorporated herein by reference in its entirety.

In some embodiments, methods of enhancing the effects of a biocide are disclosed, comprising the step of administering an active compound in combination with a biocide, the active compound being administered in an amount effective to enhance the effects of the biocide.

"Administering" or "administration of" an active compound and/or biocide as used herein in inclusive of contacting, applying, etc. (e.g., contacting with an aqueous solution, contacting with a surface (e.g., a hospital surface such as a table, instrumentation, etc.)), in addition to providing to a subject (for example, to a human or animal subject in need of treatment for a microbial infection).

"Enhancing" the effects of a biocide by administering or applying an active compound in combination with the biocide refers to increasing the effectiveness of the biocide, such that the microorganism killing and/or growth inhibition is higher at a certain concentration of the biocide administered in combination with the active compound than without. In some embodiments, a bacteria or other microorganism is "sensitized" to the effects of a biocide, such that the bacteria or other microorganism that was resistant to the biocide prior to administering or applying the active compound (e.g., little to none, or less than 20, 10, 5 or 1% are killed upon application) is rendered vulnerable to that biocide upon or after administering the active compound (e.g., greater than 20, 30, 40, 50, 60, 70, 80, 90, or 95% or more are killed).

As used herein, the administration or application of two or more compounds (inclusive of active compounds and biocides) "in combination" means that the two compounds are administered or applied closely enough in time that the administration, application of or presence of one alters the biological effects of the other. The two compounds may be administered or applied simultaneously (concurrently) or sequentially.

Simultaneous administration or application of the compounds may be carried out by mixing the compounds prior to administration or application, or by administering or applying the compounds at the same point in time but at different anatomic sites or using different routes of administration or application, or administered or applied at times sufficiently close that the results observed are indistinguishable from those achieved when the compounds are administered or applied at the same point in time.

Sequential administration or application of the compounds may be carried out by administering or applying, e.g., an active compound at some point in time prior to administration or application of a biocide, such that the prior administration of active compound enhances the effects of the biocide (e.g., percentage of microorganisms killed and/or slowing the growth of microorganisms). In some embodiments, an active compound is administered or applied at some point in time prior to the initial administration of a biocide. Alternatively, the biocide may be administered at some point in time prior to the administration or application of an active compound, and optionally, administered or applied again at some point in time after the administration or application of an active compound.

Also disclosed is a method of controlling biofilm formation wherein the biofilm comprises Gram-negative or Gram-positive bacteria. As known in the art, "Gram-negative" bacteria are those that do not retain crystal violet dye after an alcohol wash in the Gram staining protocol, while "Gram-positive" bacteria are those that are stained dark blue or violet color after an alcohol wash in the Gram staining protocol. This is due to structural properties in the cell walls of the bacteria. Gram-positive bacteria retain the crystal violet color due to a high amount of peptidoglycan in the cell wall.

Many genera and species of Gram-negative and Gram-positive bacteria are pathogenic. A "genus" is a category of biological classification ranking between the family and the species, comprising structurally or phylogenetically related species, or an isolated species exhibiting unusual differentiation. It is usually designated by a Latin or latinized capitalized singular noun. Examples of genera of biofilm-forming bacteria affected by active compounds of this invention include, but are not limited to, *Pseudomonas, Bordetella, Vibrio, Haemophilus, Halomonas*, and *Acinetobacter*.

"Species" refer to a category of biological classification ranking below the genus, and comprise members that are structurally or phylogenetically related, or an isolated member exhibiting unusual differentiation. Species are commonly designated by a two-part name, which name includes the capitalized and italicized name of the genus in which the species belongs as the first word in the name, followed by the second word that more specifically identifies the member of the genus, which is not capitalized. Examples of species of bacteria capable of forming biofilms that are affected by active compounds of the present invention include *Pseudomonas aeuroginosa, Bordetella bronchiseptica, Bordetella pertussis, Staphylococcus aureus, Vibrio vulnificus, Haemophilus influenzae, Halomonas pacifica*, and *Acinetobacter baumannii*.

Gram-negative bacteria include members of the phylum proteobacteria, which include genus members *Escherichia, Salmonella, Vibrio*, and *Helicobacter*. Other examples of Gram-negative bacteria include, but are not limited to, bacteria of the genera *Klebsiella, Proteus, Neisseria, Helicobacter, Brucella, Legionella, Campylobacter, Francisella, Pasteurella, Yersinia, Bartonella, Bacteroides, Streptobacillus, Spirillum, Moraxella* and *Shigella*.

Examples of Gram-positive bacteria include, but are not limited to, bacteria of the genera *Listeria, Staphylococcus, Streptococcus, Bacillus, Corynebacterium, Enterococcus, Peptostreptococcus*, and *Clostridium*. Species examples include, but are not limited to, *Listeria monocytogenes, Staphylococcus aureus* (including methicillin-resistant *S. aureus*, or MRSA), *Staphylococcus epidermidis, Streptococcus pyogenes, Streptococcus pneumoniae, Bacillus cereus, Bacillus anthracia, Clostridium botulinum, Clostridium perfringens, Clostridium difficile, Clostridium tetani, Corynebacterium diphtheriae, Corynebacterium ulcerans, Enterococcus faecium* (including vancomycin-resistant *E. faecium*, or VRE), and *Peptostreptococcus anaerobius*.

Additional bacteria genera in which compounds disclosed herein may be useful in controlling biofilms include, but are not limited to, *Actinomyces, Propionibacterium, Nocardia* and *Streptomyces*. *Actinomyces* is a Gram-positive genus that includes opportunistic pathogens in humans and animals, e.g., in the oral cavity, and can cause actinomycosis (caused by, e.g., *Actinomyces israelii*). *Propionibacterium acnes* is a Gram-positive species that can cause acne and chronic blepharitis and endophthalmitis (e.g., after intraocular surgery). *Nocardia* is a Gram-positive genus that includes opportunistic pathogenic species causing, e.g., slowly progressive pneumonia, encephalitis, etc. *Streptomyces* is a Gram-positive genus that occasionally are found in human infections, such as mycetoma (caused by, e.g., *S. somaliensis* and *S. sudanensis*).

A method for treating a chronic bacterial infection in a subject in need thereof is disclosed, comprising administering active compound to said subject in an amount effective to inhibit, reduce, or remove a biofilm component of said chronic bacterial infection. "Treating" as used herein refers to any type of activity that imparts a benefit to a patient afflicted with a disease, including improvement in the condition of the patient (e.g., in one or more symptoms), delay in the progression of the disease, delay in onset of the disease, etc. Though the present invention is primarily concerned with the treatment of human subjects, the invention may also be carried out on animal subjects, particularly mammalian subjects (e.g., mice, rats, dogs, cats, rabbits, and horses), avian subjects (e.g., parrots, geese, quail, pheasant), livestock (e.g., pigs, sheep, goats, cows, chickens, turkey, duck, ostrich, emu), reptile and amphibian subjects, for veterinary purposes or animal husbandry, and for drug screening and drug development purposes.

A "chronic bacterial infection" is a bacterial infection that is of a long duration or frequent recurrence. For example, a chronic middle ear infection, or otitis media, can occur when the Eustachian tube becomes blocked repeatedly due to allergies, multiple infections, ear trauma, or swelling of the adenoids. The definition of "long duration" will depend upon the particular infection. For example, in the case of a chronic middle ear infection, it may last for weeks to months. Other known chronic bacterial infections include urinary tract infection (most commonly caused by *Escherichia coli* and/or *Staphylococcus saprophyticus*), gastritis (most commonly caused by *Helicobacter pylori*), respiratory infection (such as those commonly afflicting patents with cystic fibrosis, most commonly caused by *Pseudomonas aeruginosa*), cystitis (most commonly caused by *Escherichia coli*), pyelonephritis (most commonly caused by *Proteus* species, *Escherichia coli* and/or *Pseudomonas* species), osteomyelitis (most commonly caused by *Staphylococcus aureus*, but also by *Escherichia coli*), bacteremia, skin infection, rosacea, acne, chronic wound infection, infectious kidney stones (can be caused by *Proteus mirabilis*), bacterial endocarditis, and sinus infection. A common infection afflicting pigs is atrophic rhinitis (caused by *Bordatella* species, e.g. *Bordatella bronchiseptica, Bordatella rhinitis*, etc.).

Various nosocomial infections that are especially prevalent in intensive care units implicate *Acinetobacter* species such as *Acinetobacter baumannii* and *Acinetobacter lwoffi*. *Acinetobacter baumanni* is a frequent cause of nosocomial pneumonia, and can also cause skin and wound infections and bacteremia. *Acinetobacter lwoffi* causes meningitis. The *Acinetobacter* species are resistant to many classes of antibiotics. The CDC has reported that bloodstream infections implicating *Acinetobacter baumanni* were becoming more prevalent among service members injured during the military action in Iraq and Afghanistan.

*Staphylococcus aureus* is a common cause of nosocomial infections, often causing post-surgical wound infections. *Staphylococcus aureus* can also cause variety of other infections in humans (e.g., skin infections), and can contribute to mastitis in dairy cows. *Staphylococcus aureus* has become resistant to many of the commonly used antibiotics.

E. DEVICES

Medical devices comprising a substrate and an effective amount of active compound are also disclosed. "Medical device" as used herein refers to an object that is inserted or implanted in a subject or applied to a surface of a subject. Common examples of medical devices include stents, fasteners, ports, catheters, scaffolds and grafts. A "medical device substrate" can be made of a variety of biocompatible materials, including, but not limited to, metals, ceramics, polymers, gels, and fluids not normally found within the human body. Examples of polymers useful in fabricating medical devices include such polymers as silicones, rubbers, latex, plastics, polyanhydrides, polyesters, polyorthoesters, polyamides, polyacrylonitrile, polyurethanes, polyethylene, polytetrafluoroethylene, polyethylenetetraphthalate, etc.

Medical devices can also be fabricated using naturally-occurring materials or treated with naturally-occurring materials. Medical devices can include any combination of artificial materials, e.g., combinations selected because of the particular characteristics of the components. Medical devices can be intended for short-term or long-term residence where they are positioned. A hip implant is intended for several decades of use, for example. By contrast, a tissue expander may only be needed for a few months, and is removed thereafter.

Some examples of medical devices are found in U.S. Pat. No. 7,081,133 (Chinn et al.); U.S. Pat. No. 6,562,295 (Neuberger); and U.S. Pat. No. 6,387,363 (Gruskin); each incorporated by reference herein in its entirety.

F. AGRICULTURAL METHODS OF USE

In some embodiments, target crops or plants to be treated with active compounds and compositions of the invention may include the following plants: cereal (wheat, barley, rye, oat, rice, maize, sorghum and related species); beet (sugar beet and fodder beet); pomes, drupes and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (pumpkins, cucumbers, melons); fiber plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocado, cinnamon, camphor) or plants such as tobacco, nuts, coffee, eggplants, sugar cane, tea, pepper, vines including grape-bearing vines, hops, bananas, pineapple, turf and natural rubber plants, as well as ornamentals (flowers, shrubs, broad-leafed trees and evergreens, such as conifers). This list does not represent any limitation.

1. Bacterial Infections.

The methods, active compounds and compositions can be used to treat bacterial infections in a variety of plants, with specific examples including but not limited to those set forth below.

Citrus.

In citrus trees (including orange, lemon, lime, and grapefruit) active compounds and compositions as described herein can be used to treat or control a variety of microbial diseases, including but not limited to canker (caused by *Xanthomonas campestris* or *Xanthomonas axonopodis* infection), bacterial spot (caused by *Xanthomonas campestris* pv. *Citrumelo* infection); Black Pit (fruit) (caused by *Pseudomonas syringae* infection); Blast (caused by *Pseudomonas syringae* infection) citrus variegated chlorosis (caused by *Xylella fastidiosa* infection), and Citrus Huanglongbing (HLB) caused by *Candidatus Liberibacter asiaticus*.

Pome Fruit.

In pome fruits (including apple, pear, quince, Asian pear, and loquat), active compounds and compositions as described herein can be used to treat or control a variety of microbial infections, including but not limited to Fire Blight (caused by *Erwinia amylovora* infection), Crown Gall (caused by *Agrobacterium tumefaciens* infection); Blister spot (caused by *Pseudomonas syringae* infection) and Hairy root (caused by *Agrobacterium rhizogenes* infection).

Peppers.

In pepper plants, active compounds and compositions as described herein can be used to treat or control a variety of microbial infections, including but not limited to: Bacterial Spot (caused by *Xanthomonas campestris* pv. *vesicatoria* infection); Bacterial wilt (caused by *Ralstonia solanacearum* infection), and Syringae seedling blight and leaf spot (caused by *Pseudomonas sryingae* infection).

Tomatoes.

In tomato plants, active compounds and compositions as described herein can be used to treat or control a variety of microbial infections, including but not limited to: Bacterial canker (caused by *Clavibacter michiganesis*), Bacterial speck (caused by *Pseudomonas syringae*), Bacterial spot (caused by *Xanthomonas campestris vesicatoria*), Bacterial stem rot and fruit rot (caused by *Erwinia carotovora*), Bacterial wilt (caused by *Ralstonia solanacearum*), Pith necrosis (caused by *Pseudomonas corrugate*), and Syringae leaf spot (caused by *Pseudomonas syringae*).

Soybeans.

In soybeans, active compounds and compositions as described herein can be used to treat or control a variety of microbial infections, including but not limited to: Bacterial blight (caused by *Pseudomonas amygdale*), Bacterial pustules (caused by *Xanthomonas axonopodis* pv. *Glycines*), and Bacterial wilt (caused by *Ralstonia solanacearum* or *Curtobacterium flaccumfaciens*).

Corn, Cotton, Wheat and Rice.

In corn, cotton, wheat and rice, active compounds and compositions as described herein can be used to treat or control a variety of microbial infections, including but not limited to: bacterial blights, leaf spots and leaf streak caused by *Xanthomonas* species; bacterial sheath rot, stripe and spot caused by *Pseudomonas* species; and to bacterial stalk and top rot, wilt, foot rot, pink seed and lint degradation caused by *Erwinia* species.

Pineapple.

In pineapple, active compounds and compositions as described herein can be used to treat or control a variety of microbial infections, including but not limited to: Bacterial heart rot and Fruit collapse (caused by *Erwinia chrysanthemi*), Bacterial fruitlet brown rot (caused by *Erwinia ananas*), Marbled fruit and Pink fruit (caused by *Erwinia herbicola*), Soft rot (caused by *Erwinia carotovora*), and Acetic souring (caused by Acetic acid bacteria).

The above listing is but a sampling, and active compounds and compositions as described herein may also be used to treat or control bacteria (some of which are named above) in a variety of plants. For example, the bacteria *Xylella fastidiosa* infects citrus trees as noted above (citrus variegated chlorosis), and also infects grapevines (Pierce's disease). Other plant hosts of *Xylella fastidiosa* include, but are not limited to, ornamentals, oleander (leaf scorch), almond, coffee, maple, mulberry, elm, sycamore, alfalfa, etc. Similarly, *Ralstonia solanacearum* infects soybeans (bacterial wilt) as well as banana (Moko disease), tobacco (Granville wilt), geranium (southern bacterial wilt), potato (brown rot) and a wide variety of other plants, including ginger and mulberry.

2. Fungal Infections.

In addition to treating or controlling bacterial infections, active compounds and compositions as described herein can be used to treat or control fungal infections such as rots, leaf molds, blights, wilts, damping-off, spot, root rot, stem rot, mildew, brown spot, gummosis, melanose, post-bloom fruit drop, scab, alternaria, canker, flyspeck, fruit blotch, dieback, downy mildews, ear rots, anthracnose bunts, smut, rust, eyespot and pecky rice. Genera of plant-pathogenic fungi that can be treated or controlled by the active compounds, compositions, and methods described herein include but are not limited to: *Pythium* spp., *Fusarium* spp., *Rhizoctonia* spp., *Cercospora* spp., *Alternaria* spp., *Colletotrichum* spp., *Ustilago* spp., *Phoma* spp., *Gibberella* spp. *Penicillium* spp., *Glomerella* spp. *Diplodia* spp., *Curvularia* spp., *Sclerospora* spp., *Peronosclerospora* spp., *Cercospora* spp., *Puccinia* spp., *Ustilago* spp., *Aspergillus* spp., *Phomopsis* spp., *Diaporthe* spp., *Botrytis* spp., *Verticillium* spp., *Phytophthora* spp.

Particular fungal infections that can be treated or controlled by the methods, compounds and compositions described herein, in vegetables and greenhouse crops, include *Phytophthora* blight (caused by *Phytophthora capsici*) and *Pythium* damping-off (caused by *Pythium* spp).

Note that *Phytophthora* also has adverse effects on crops ranging from pineapples to cotton. It can kill woody citrus seedlings and young citrus trees (oranges, grapefruits, lemons, limes). In the greenhouse, germinating seed and seedlings are very susceptible to damping-off caused by *Phytophthora, Pythium, Sclerotina* and *Rhizoctonia* species. The cost to the grower to lose his crop to any of these fungi is substantial. The loss can happen at transplant time or when the crop is ready to be harvested.

The problems of fungi are not restricted to traditional crops but also extend to forestry products and have worldwide scope. *Phytophthora cinnamomi* is a soil-borne water mould that leads to a condition in plants called "root rot" or "dieback." *P. cinnamomi* causes root rot affecting woody ornamentals including azalea, dogwood, forsythia, Fraser fir, hemlock, Japanese holly, juniper, rhododendron, white pine, and American chestnut. *P. cinnamomi* is responsible for the destruction of the elegant American chestnut tree. In Australia, *P. cinnamomi* has spread through the forests of western Australia, and into coastal forests of Victoria, where entire plant ecosystems are being obliterated. Given that *P. cinnamomi* is a soil-borne water mould that infects the roots, almost the entire action takes place below ground. This problem highlights the importance of developing new compounds to counter fungal infections, even those that directly affect only the roots of the plant rather than the more visible effects on fruits or vegetables.

Active compounds of the invention can be applied to plants or plant loci in accordance with known techniques. The compound(s) can be tank mixed with other agricultural, turf, ornamental nursery, forestry and all other plant-labeled compatible pesticides. The compound(s) can be applied to seed. The compound(s) can be applied to edible and non-edible crops. The compound(s) can be applied to roots and all other parts of all plants. The compound(s) can be applied in greenhouses. The compound(s) can be applied and used in food-processing facilities. The compound(s) can be applied to plastic food bags and containers. The compound(s) can be applied as a solid, as its free base, or as a salt. The salts can include, but are not limited to, HI, HCl, HBr, $H_2SO_4$, acetic acid, and trifluoroacetic acid. The compound(s) can applied as a solution from 0.0001% to 99.9%. The compound(s) can be applied as a solid or solution with copper-based cidal compounds. The compound(s) can be applied with specific additional active agents, including but not limited to bactericides, fungicides, pesticides, biological insecticides and microbial insecticides.

Application can be carried out with any suitable equipment or technique, such as: Aerial—Fixed wing and Helicopter; Ground Broadcast Spray—Boom or boomless system, pull-type sprayer, floaters, pick-up sprayers, spray coupes, speed sprayers, and other broadcast equipment, water wagons and water bags; Low pressure boom sprayers, High pressure sprayers; Air blast sprayers; Low volume air sprayers (mist blowers); Ultra-low volume sprayers (ULV);

Aerosol Generators (foggers); Dusters; Soil Injector; Hand-Held or High-Volume Spray Equipment—knapsack and backpack sprayers, pump-up pressure sprayers, hand guns, motorized spray equipment; Selective Equipment—Recirculating sprayers, shielded and hooded sprayers; Controlled droplet applicator (CDA) hand-held or boom-mounted applicators that produce a spray consisting of a narrow range of droplet size; Any and all greenhouse sprayers; Microsprinkler or drip irrigation systems; Chemigation.

One method of applying an active compound of the invention, or an agrochemical composition which contains at least one of said compounds, is foliar application. The frequency of application and the rate of application will depend on the risk of infestation by the corresponding pathogen. However, the active compounds can also penetrate the plant through the roots via the soil (systemic action) by drenching the locus of the plant with a liquid formulation, or by applying the compounds in solid form to the soil, e.g. in granular form (soil application). In crops of water such as rice, such granulates can be applied to the flooded rice field. The active compounds may also be applied to seeds (coating) by impregnating the seeds or tubers either with a liquid formulation of the fungicide or coating them with a solid formulation.

The term locus as used herein is intended to embrace the fields on which the treated crop plants are growing, or where the seeds of cultivated plants are sown, or the place where the seed will be placed into the soil. The term seed is intended to embrace plant propagating material such as cuttings, seedlings, seeds, and germinated or soaked seeds.

Advantageous rates of application are normally from 5 g to 2 kg of active ingredient (a.i.) per hectare (ha), preferably from 10 g to 1 kg a.i./ha, most preferably from 20 g to 600 g a.i./ha. When used as seed drenching agent, convenient dosages are from 10 mg to 1 g of active substance per kg of seeds.

In some embodiments, methods of enhancing the effects of a biocide (such as a microbicide comprising copper, e.g., Kocide® 2000 or Kocide® 3000 (DuPont™, with active ingredient copper hydroxide) are disclosed, comprising the step of applying an active compound in combination with a microbicide, the active compound being applied in an amount effective to enhance the effects of the microbicide.

In some embodiments, methods of enhancing the effects of a plant defense activator are disclosed, comprising the step of applying an active compound in combination with a plant defense activator, the active compound being applied in an amount effective to enhance the effects of the plant defense activator. Similar to enhancing the effects of a biocide noted above, "enhancing" the effects of a plant defense activator by applying an active compound in combination with the plant defense activator refers to increasing the effectiveness of the plant defense activator, such that the microorganism killing and/or growth inhibition is higher at a certain concentration of the plant defense activator applied in combination with the active compound than without. In some embodiments, a bacteria or other microorganism is "sensitized" to the effects of a plant defense activator, such that the bacteria or other microorganism that was resistant to the effects of the plant defense activator prior to applying the active compound (e.g., little to none, or less than 20, 10, 5 or 1% are killed upon application) is rendered vulnerable to the effects of that plant defense activator upon or after applying the active compound (e.g., greater than 20, 30, 40, 50, 60, 70, 80, 90, or 95% or more are killed).

G. COVALENT COUPLING OF ACTIVE COMPOUNDS

In some embodiments, active compounds as described herein are covalently coupled to substrates. Examples of substrates include solid supports and polymers. The polymers, typically organic polymers, may be in solid form, liquid form, dispersed or solubilized in a solvent (e.g., to form a coating composition as described above), etc. The solid support may include the substrate examples as described above to be coated with or treated with active compounds of the invention.

Covalent coupling can be carried out by any suitable technique. Active compounds of the present invention may be appended to a substrate via aldehyde condensation, amine bond, amide or peptide bond, carbon-carbon bond, or any suitable technique commonly used in the art. See also U.S. Patent Application Publication No. 2008/0181923 to Melander et al., which is incorporated by reference herein. A preferred method according to some embodiments is amine or amide bond formation. Further examples and explanations of these types of reactions can be found in U.S. Pat. No. 6,136,157 (Lindeberg et al.) and U.S. Pat. No. 7,115,653 (Baxter et al.), which are each hereby incorporated by reference in their entirety.

Various coupling reactions can be used to covalently link active compounds of the present invention to a substrate. Examples of coupling reactions that can be used include, but are not limited to, Hiyama, Suzuki, Sonogashira, Heck, Stille, Negishi, Kumada, Wurtz, Ullmann, Cadiot-Chodkiewicz, Buchwald-Hartwig, and Grignard reactions. For example, an active compound that is substituted with a halide (e.g. bromo or chloro) can be coupled to a substrate via a Heck reaction.

Some aspects of the present invention are described in more detail in the following non-limiting examples.

EXAMPLE 1

A library of 4,5-disubstituted-2-aminoimidazoles was synthesized using a nitroenolate route and then screened for antibiofilm and antimicrobial activity. These compounds displayed notable biofilm dispersal and planktonic microbicidal activity against various Gram-positive and Gram-negative bacteria.

The synthesis of 4,5-disubstituted-2-aminoimidazoles was accomplished via a nitroenolate approach (Scheme 1) because the starting building blocks, activated carboxylic acids and alkyl nitro derivatives, are either commercially available or available in one step from either carboxylic acids or alkyl halides respectively. Once assembled, the target α-nitro ketones could simply be reduced and then condensed with cyanamide to yield 4,5-disubstituted-2-aminoimidazoles. See Ballini et al., Tetrahedron, 2005, 61, 8971-8993.

Scheme 1. 4,5-disubstituted-2-aminoimidazole synthetic route.

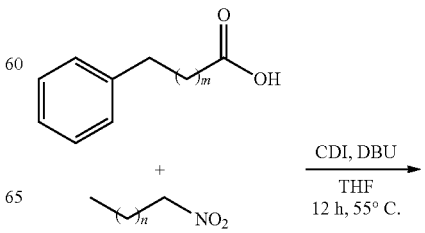

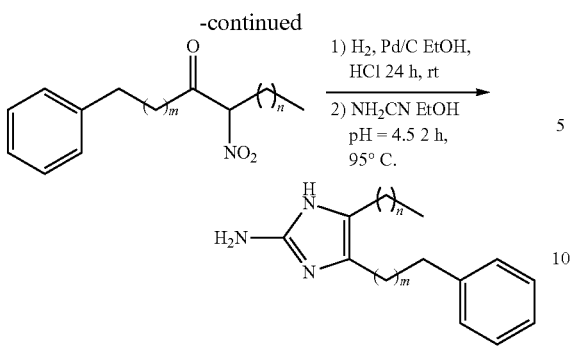

This synthetic approach was first optimized by using 4-phenylbutryic acid and nitromethane as the building blocks. A combination of enolization base, carboxylate activation and solvent were determined that would deliver the highest yield of the targeted α-nitro ketone. THF and $CH_2Cl_2$ were screened as potential solvents, DBU and t-BuO⁻K⁺ as enolization bases, and CDI and ethyl chloroformate as carboxylate activators. From this initial screen, it was determined that 2.5 equivalents of DBU as the enolazization base, THF as the solvent and CDI as the activating agent generated the target α-nitro ketone in the highest yield (76%) when the reaction was run at 40° C. overnight.

Once the conditions of the nitroenolate approach had been determined, these conditions were applied to the synthesis of 4,5-disubstituted-2-aminoimidazoles, first to the coupling of 4-phenylbutryic acid and 1-nitropropane. Under these conditions, access the target α-nitro ketone was accessed in a 27% yield. The reaction was further optimized by varying the reaction temperature and reaction time (Table 1). The temperature was first varied from room temperature to reflux (66° C., entries 1-5) and the optimal temperature was determined to be 55° C. Heating the reaction to higher temperatures led to a decreased reaction yield, most likely from decomposition. It was then determined if reaction time would affect reaction yield by running the reaction for either 6, 12, 24, or 48 hours. As predicted by our temperature studies, the longer the reaction is heated, the lower the yield of the target α-nitro ketone. At 6 hours, the reaction yield was slightly lower. Under these optimal conditions (2.5 eq. DBU, 2 eq. CDI, THF, 55° C., 12 hours), a 50% yield of the target α-nitro ketone was achieved.

TABLE 1

Effects of reaction time and temperature on product yield.

| Entry | T/° C. | Time/h | Yield [%] |
|---|---|---|---|
| 1 | RT | 12 | 20 |
| 2 | 40 | 12 | 27 |
| 3 | 45 | 12 | 47 |
| 4 | 50 | 12 | 46 |
| 5 | 55 | 12 | 50 |
| 6 | 66 | 12 | 20 |
| 7 | 55 | 6 | 43 |
| 8 | 55 | 24 | 24 |
| 9 | 55 | 48 | — |

Once the α-nitro ketone was obtained, it was verified that the reduction/condensation sequence would deliver the target 2-aminoimidazole. The nitro group was reduced to the corresponding amine using $H_2$, 5 eq. HCl and 5% Pd/C in ethanol. The resulting crude reaction was then filtered over celite, and the ethanol and excess HCl removed in vacuo to deliver the crude α-amino ketone as its HCl salt. The salt was then redissolved in ethanol, 5 eq. cyanamide was then added, the pH adjusted to 4.5, and the resulting solution was heated to 95° C. for two hours. After purification, the target 4,5-disubstituted 2-aminoimidazole was isolated in 55% yield.

Using this approach, a 15-member pilot library was assembled where both the length of the alkyl chain and the number of methylene units between the 2-aminoimidazole and phenyl group were varied (Table 2).

TABLE 2

Composition of pilot library.

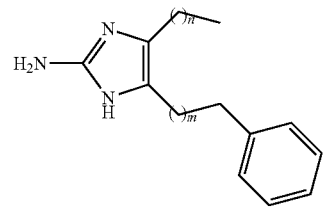 [SMILES: CCc1nc(N)[nH]c1CCc1ccccc1]

| Compound | n = | m = |
|---|---|---|
| 1 | 0 | 2 |
| 2 | 1 | 2 |
| 3 | 2 | 2 |
| 4 | 3 | 2 |
| 5 | 4 | 2 |
| 6 | 0 | 3 |
| 7 | 1 | 3 |
| 8 | 2 | 3 |
| 9 | 3 | 3 |
| 10 | 4 | 3 |
| 11 | 0 | 4 |
| 12 | 1 | 4 |
| 13 | 2 | 4 |
| 14 | 3 | 4 |
| 15 | 4 | 4 |

Biological Screening

The ability of each member of the pilot library to inhibit either *E. coli* or MDRAB biofilm formation at 100 μM was assessed using a crystal violet reporter assay (O'Toole et al., *Mol. Microbiol.*, 1998, 30: 295-304). The results of this initial screen are summarized in Table 3. From this screen, 12 compounds inhibited *E. coli* biofilm formation >95%, while eight compounds inhibited MDRAB biofilm formation >95%.

TABLE 3

Test compound inhibition of biofilm formation at 100 μM.

| Compound | *E. coli* | MDRAB |
|---|---|---|
| 1 | <5 | <5 |
| 2 | >99 | >99 |
| 3 | >99 | >99 |
| 4 | >99 | >99 |
| 5 | >99 | >99 |
| 6 | >99 | >99 |
| 7 | 86.4 ± 7.9 | 72.9 ± 0.4 |
| 8 | 97.9 ± 0.6 | 96.5 ± 2.6 |
| 9 | 98.2 ± 0.03 | >99 |
| 10 | 96.6 ± 2.9 | 94.3 ± 2.2 |
| 11 | 96.3 ± 0.08 | >99 |
| 12 | >99 | 94.5 ± 0.2 |
| 13 | 95.8 ± 1.5 | 87.8 ± 0.3 |
| 14 | 96.9 ± 1.1 | 85.4 ± 0.7 |
| 15 | 83.0 ± 0.8 | 80.3 ± 8.1 |

When each compound that showed >80% activity was subjected to a dose-response study to determine the $IC_{50}$ value for biofilm inhibition, it was noted that biofilm inhibition dropped precipitously over a narrow concentration range. This is typically indicative of biofilm inhibition via a traditional microbicidal mechanism instead of a mechanism that modulates biofilm formation through non-microbicidal mechanisms. The microbicidal activity of representative compound 15 was verified by conducting a growth curve analysis ($A_{600}$) against *E. coli* at its $IC_{50}$ concentration (13 μM). At this concentration, a 97% reduction in bacterial growth was observed.

Once it was determined that this specific 4,5-disubstitution pattern imparted microbicidal activity onto the 2-AI framework, this activity was quantified by measuring the MIC of each derivative against a variety of representative pathogenic bacterial strains using the microdilution protocol (CSLI, *Performance Standards for Antimicrobial Suceptibility Testing; Nineteenth Informational Supplement*, Clinical and Laboratory Standards Institute, Wayne, Pa., 2009). *E. coli*, MDRAB, *P. aeruginosa*, MRSA, MSSA, *S. epidermidis* and VRE were used for initial evaluation. The results of this study are outlined in Table 4. From this screen, compound 15 was determined to be the lead compound and had MIC values (μg/mL) of 2, 2, 1, 0.5, 0.25, and 1 against *E. coli*, MDRAB, MRSA, VRE, *S. Epidermidis* and MSSA. In general, it was noted that activity correlated with the length of the alkyl chain, with 5 carbons being most active. It was also observed that the linker between the 2-AI and phenyl ring also modulated activity, as the 5-carbon spacer was most active.

TABLE 4

Microdilution MIC of pilot library of compounds for representative pathogenic bacterial strains.

| Compound | *E. coli*[a] | MDRAB[a] | MRSA[a] | MSSA[a] | *S. epidermidis*[a] | VRE[a] |
|---|---|---|---|---|---|---|
| 1 | 128 | 128 | 64 | 32 | 8 | 256 |
| 2 | 32 | 32 | 16 | 8 | 2 | 16 |
| 3 | 16 | 32 | 8 | 4 | 4 | 8 |
| 4 | 32 | 64 | 16 | 16 | 4 | 16 |
| 5 | 8 | 8 | 4 | 4 | 1 | 2 |
| 6 | 32 | 16 | 8 | 2 | 0.25 | 16 |
| 7 | 32 | 32 | 32 | 16 | 4 | 32 |
| 8 | 8 | 16 | 8 | 4 | 2 | 4 |
| 9 | 32 | 32 | 8 | 8 | 2 | 4 |
| 10 | 8 | 8 | 2 | 2 | 0.5 | 1 |
| 11 | 8 | 8 | 4 | 2 | 1 | 8 |
| 12 | 16 | 32 | 8 | 4 | 2 | 8 |
| 13 | 8 | 8 | 4 | 4 | 0.5 | 4 |
| 14 | 4 | 4 | 2 | 2 | 0.25 | 2 |
| 15 | 2 | 2 | 1 | 1 | 0.25 | 0.5 |

[a]MIC values are in μg mL$^{-1}$

Once it was noted that increasing chain length of both the alkyl chain and the linker correlated with increased activity, five second generation compounds were synthesized (Table 5) these two parameters were further varied. The MIC values of the second generation compounds against each of the aforementioned bacterial strains are outlined in Table 6. None of the second generation compounds displayed augmented activity in comparison to lead compound 15; however, compound 19 had similar activity.

TABLE 5

Second generation compounds.

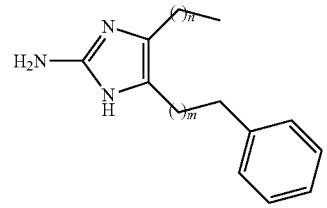 [SMILES: CCc1nc(N)[nH]c1CCc1ccccc1]

| Compound | n = | m = |
|---|---|---|
| 16 | 3 | 5 |
| 17 | 4 | 5 |
| 18 | 5 | 5 |
| 19 | 5 | 4 |
| 20 | 5 | 3 |

TABLE 6

Microdilution MIC values of second generation compounds.

| Compound | *E. coli*[a] | MDRAB[a] | MRSA[a] | MSSA[a] | *S. epidermidis*[a] | VRE[a] |
|---|---|---|---|---|---|---|
| 16 | 8 | 8 | 1 | 2 | 0.5 | 1 |
| 17 | 32 | 16 | 1 | — | — | 1 |
| 18 | 8 | 16 | 1 | 2 | 0.5 | 1 |
| 19 | 2 | 4 | 1 | 1 | 0.5 | 0.5 |
| 20 | 8 | 8 | 1 | 2 | 0.5 | 1 |

[a]MIC values are in μg mL$^{-1}$

Once the effect had been determined that these 4,5-disubstituted-2-aminoimidazoles had on representative terrestrial pathogens, their activity against a representative set of marine bacteria was determined. This was driven by a number of factors, including our interest in the development of antibiofoulants (Melander et al., *Int. Biodeter. Biodegr.*, 2009, 63: 529-532) and the prevalence of vibrio infections in human populations (Igbinosa et al., *Res. Microbiol.*, 2008, 159: 495-506). *Vibrio cholerae*, *Vibrio vulnificus*, *Listonella anguillarum* and *Rhodospirillum salexigens* were used for the evaluation. Given the microbicidal activity that was observed against terrestrial bacterial strains, the MIC values of each compound against all the aforementioned strains were determined. This data is summarized in Table 7. Paralleling the previous results, compounds 15 and 19 were the lead compounds. Compound 15 had MIC values of 4.2, 2.1, 2.1 and 2.1 μg/mL against *V. cholerae*, *V. vulnificus*, *L. anguillarum* and *R. salexigens* respectively, while compound 19 had MIC values of 2.2 μg/mL against *V. cholerae*, *V. vulnificus* and *L. anguillarum* and 1.1 μg/mL against *R. salexigens*.

TABLE 7

Marine bacteria microdilution MIC data for both pilot and second generation libraries.

| Compound | *V. cholerae*[a] | *V. vulnificus*[a] | *L. anguillarum*[a] | *R. salexigens*[a] |
|---|---|---|---|---|
| 1 | >50 | 50.4 | 50.4 | 50.4 |
| 2 | 53.2 | 26.6 | 26.6 | 13.3 |
| 3 | 27.9 | 27.9 | 13.9 | 13.9 |
| 4 | 58.8 | 58.8 | 58.8 | 29.4 |
| 5 | 15.4 | 15.4 | 7.70 | 3.85 |
| 6 | 26.6 | 26.6 | 13.9 | 13.3 |

TABLE 7-continued

Marine bacteria microdilution MIC data for both pilot and second generation libraries.

| Compound | V. cholerae[a] | V. vulnificus[a] | L. anguillarum[a] | R. salexigens[a] |
|---|---|---|---|---|
| 7 | 55.9 | 13.9 | 13.9 | 13.9 |
| 8 | 29.4 | 14.7 | 14.7 | 7.35 |
| 9 | 30.8 | 30.8 | 30.8 | 7.70 |
| 10 | 16.1 | 8.05 | 8.05 | 2.01 |
| 11 | 27.9 | 13.9 | 13.9 | 7.00 |
| 12 | 29.4 | 29.4 | 14.7 | 14.7 |
| 13 | 15.4 | 3.85 | 7.70 | 3.85 |
| 14 | 8.05 | 4.02 | 4.02 | 8.05 |
| 15 | 4.20 | 2.10 | 2.10 | 2.10 |
| 16 | 8.40 | 8.40 | 4.20 | 2.10 |
| 17 | 69.9 | 69.9 | 69.9 | 69.9 |
| 18 | 18.2 | 18.2 | 18.2 | 2.27 |
| 19 | 2.19 | 2.19 | 2.19 | 1.09 |
| 20 | 4.20 | 4.20 | 4.20 | 2.10 |

[a]MIC values are in µg mL$^{-1}$

The ability of 15 and 19 to disperse pre-formed biofilms was also determined for all of the aforementioned bacterial strains (both marine and terrestrial). To quantify this effect, the $EC_{50}$ value of each compound against each bacterial strain was determined, where $EC_{50}$ is defined as the concentration of compound that elicits 50% dispersion of a pre-formed biofilm. This data is summarized in Table 8. Both compounds are able to disperse pre-formed biofilms at low micromolar concentrations. These concentrations are also microbicidal to planktonic bacteria.

TABLE 8

Marine bacteria biofilm dispersion data for lead compounds.

| Compound | 15[a] | 19[a] |
|---|---|---|
| E. coli | 12.0 ± 1.6 | 42.5 ± 6.1 |
| MDRAB | 7.1 ± 1.3 | 11.1 ± 0.1 |
| MRSA | 33.9 ± 3.9 | 74.9 ± 9.8 |
| MSSA | 19.9 ± 3.3 | 26.1 ± 0.7 |
| S. epidermidis | 24.7 ± 5.8 | 17.7 ± 0.3 |
| VRE | 17.3 ± 2.3 | 14.1 ± 0.2 |
| V. cholerae | 7.12 ± 0.3 | 14.7 ± 1.8 |
| V. vulnificus | 18.1 ± 2.3 | 3.20 ± 1.3 |
| L. anguillarum | 14.7 ± 1.7 | 13.8 ± 1.5 |
| R. salexigens | 6.60 ± 1.1 | 17.6 ± 3.2 |

[a]$EC_{50}$ values are in µM

To examine the necessity of the 4,5-disubstitution pattern for antimicrobial activity of the 2-aminoimidazole scaffold, two monosubstituted 2-aminoimidazole analogues of compound 19 were synthesized and screened alongside the parent 2-aminoimidazole for antibiotic activity (Scheme 2). Heptanoic acid and phenylhexanoic acid were treated with oxalyl chloride with catalytic dimethyl formamide in dichloromethane to produce the respective acid chlorides, which were then reacted with diazomethane and quenched with hydrobromic acid to make the respective alpha-bromo ketones. These alpha-bromo ketones were separately cyclized with boc-guanidine, providing a boc-protected 2-aminoimidazole scaffold that was subsequently deprotected upon treatment with trifluoroacetic acid in dichloromethane to yield 22 and 23.

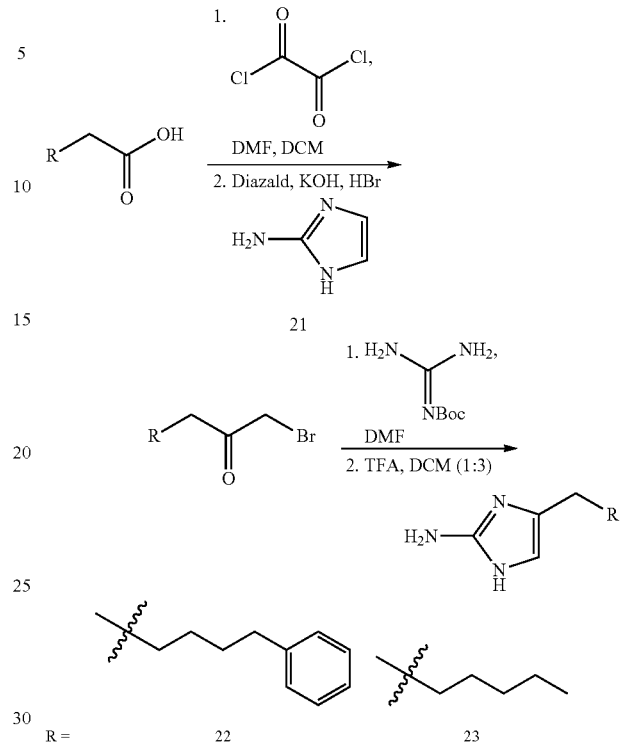

2-aminoimidazole 21, was found to have no antibiotic activity at the highest concentration tested (36 µg/mL) against every bacterial strain. Compound 22 demonstrated MIC values of greater than 41 µg/mL against all of the test strains except for S. epidermidis in which a remarkable MIC value of 0.04 µg/mL was found; making 22 the most potent antibiotic in this study. Lastly, compound 23 was also found to contain no notable antibiotic activity against any of the test strains except for S. epidermidis for which an MIC value of 0.05 µg/mL was found. This demonstrates the necessity for substitution on the 2-AI scaffold to elicit the antibiotic response with broad spectrum activity being attributed to 4,5-disubstitution.

Once the anti-biofilm and antibacterial properties of each 2-AI derivative had both been evaluated, the hemolytic potential of compounds 15, 19 and 1 was assessed (Liu et al., *Antimicrob. Agents. Ch.,* 2007, 51: 597-603). Compounds 15 and 19 are the leads from the first generation and second generation compounds, respectively, while compound 1 was used for comparison purposes to evaluate the activity of a bacterial inactive 2-AI. Hemolysis was measured using difibrinated sheep's blood. Hemolytic potential was quantified by determining the $HD_{50}$ of compound 15, 19 and 1, where $HD_{50}$ is defined as the concentration that elicits 50% hemolysis. From this assay, we determined that the $HD_{50}$ of compound 15, 19 and 1 were 66 µM, 61 µM and >400 µM. This corresponds to 22 and 21 µg/mL for compounds 15 and 19.

Finally, given that active compounds are characterized by a polar head group and a lipophilic tail, it was probed whether compounds 15 and 19 were eliciting their activity via a pore forming mechanism. Compound 1 was used as a control. This was probed via a dye dispersion assay from synthetic vesicles (Liu et al., *J. Am. Chem. Soc.,* 2001, 123, 7553-7559). Two types of vesicles were prepared, one containing 1-palmitoyl-2-oleoyl-sn-glycero-3-phosphocholine (POPC) and the other containing 1-palmitoyl-2-oleoyl-sn-glycero-3-phosphoglycerol (POPG). POPC mimics typical cell membranes encountered for mammalian red blood cells, while POPG mimics the negatively charged lipids encountered in bacterial membranes. In 5 minutes, at 25 µM, compounds 15 and 19 elicited 20% dye leakage from the POPG vesicles while they elicited 10% and 15% dye leakage from the POPC vesicles respectively. However, in 5 minutes at 500 µM, compounds 15 and 19 elicited 78% and 85% dye leakage from the POPG vesicles respectively. In 5 minutes at 25 µM, control compound 1 elicited 9% and 18% leak dye leakage from the POPC and POPG vesicles respectively, while in 5 minutes at 500 µM 1 elicited 15% and 50% leakage from the POPC and POPG vesicles. Given this differential response, and without wishing to be bound by theory, it is likely that compounds 15 and 19 are inducing microbicidal activity through a simple pore-forming mechanism.

Experimental

All reagents used for chemical synthesis were purchased from commercially available sources and used without further purification. Chromatography was performed using 60 Å mesh standard grade silica gel from Sorbtech (Atlanta, Ga., USA). NMR solvents were obtained from Cambridge Isotope Labs and used as received. $^1$H NMR (300 MHz or 400 MHz) and $^{13}$C NMR (75 MHz or 100 MHz) spectra were recorded at 25° C. on Varian Mercury spectrometers. Chemical shifts (δ) are given in ppm relative to tetramethylsilane or the respective NMR solvent; coupling constants (J) are in Hertz (Hz). Abbreviations used are s=singlet, bs=broad singlet, d=doublet, dd=doublet of doublets, t=triplet, dt=doublet of triplets, td=triplet of doublets, bt=broad triplet, q=quartet, m=multiplet, bm=broad multiplet and br=broad. Mass spectra were obtained at the NCSU Department of Chemistry Mass Spectrometry Facility.

*S. aureus* (ATCC #29213), *S. epidermidis* (ATCC #29886), MRSA (ATCC # BAA-44), MDRAB (ATCC # BAA-1605), vancomycin resistant *Enterococcus faecium* (VRE) (ATCC #51559) and *E. coli* (ATCC #35695) were obtained from the ATCC. Mechanically difibrinated sheep blood (DSB100) was obtained from Hemostat Labs. Mueller-Hinton medium was purchased from Fluka (#70192).

Synthesis of 4, 5-disubstituted 2-aminoimidazoles

General Procedure for the Preparation of α-Nitro Ketones

To a vial (23×85 mm) was added appropriate phenyl carboxylic acids and 1,1'-carbonyldiimidazole in THF (3 mL) and stirred at room temperature for 20 min. A mixture of appropriate nitroalkanes and 1,8-diazabicyclo[5.4.0]undec-7-ene, dissolved in THF (2 mL) that was pre-stirred for 20 min, was then added dropwise to the resulting solution. The resulting mixture was stirred for 12 hours at 55° C. The mixture was cooled down to 0° C. and 1N HCl (2 mL) was added, then extracted with ethyl acetate (3×2 mL). The combined organic extracts were washed with water (1×3 mL), brine (1×3 mL), dried over $Na_2SO_4$ and the solvent evaporated under reduced pressure. Purification of the residue took place on a silica-gel column and eluted with dichloromethane to give the target α-nitro ketones. Resulting α-nitro ketones judged to be >85% pure by $^1$H NMR were then subjected to hydrogenation/cyclization (detailed below). Representative α-nitro ketones and 4,5-disubstituted-2-aminoimidazoles are detailed below. All other characterization is supplied in the supplementary information.

2-nitro-8-phenyloctan-3-one

6-Phenylhexanoic acid (0.154 g, 0.80 mmol) and CDI (0.261 g, 1.60 mmol) were added together and then reacted with nitroethane (0.090 g, 1.21 mmol) and DBU (0.306 g, 2.00 mmol) according to the general procedure. Purification by column chromatography gave 0.060 g (30%) as a yellow oil: $^1$H NMR (400 MHz, $CDCl_3$) δ 7.31 (m, 2H), 7.21 (m, 3H), 5.24 (q, J=7.2 Hz, 1H), 2.64 (t, J=7.6 Hz, 2H), 2.58 (td, J=3.2, 6.8 Hz, 2H), 1.69 (d, J=7.2 Hz, 3H), 1.68 (m, 4H), 1.37 (m, 2H) ppm; $^{13}$C NMR (100 MHz, $CDCl_3$) δ 200.1, 142.6, 128.7, 128.6, 126.0, 89.1, 39.3, 35.9, 31.4, 28.7, 23.3, 15.2 ppm; IR $\nu_{max}$ ($cm^{-1}$) 3026, 2933, 2858, 1732, 1559, 1453, 1362, 1030, 749, 701; HRMS (FAB) calcd for $C_{14}H_{19}NO_3$ ($MNa^+$) 272.1257, found 272.1255.

3-nitro-9-phenylnonan-4-one

6-Phenylhexanoic acid (0.100 g, 0.52 mmol) and CDI (0.169 g, 1.04 mmol) were added together and then reacted with nitropropane (0.070 g, 0.78 mmol) and DBU (0.198 g, 1.30 mmol) according to the general procedure. Purification by column chromatography gave 0.059 g (43%) as a yellow oil: $^1$H NMR (400 MHz, $CDCl_3$) δ 7.28 (m, 2H), 7.17 (m, 3H), 5.04 (dd, J=4.4, 9.6 Hz, 1H), 2.60 (m, 4H), 1.62 (m, 6H), 1.31 (m, 2H) 1.02 (t, J=7.2 Hz, 3H) ppm; $^{13}$C NMR (100 MHz, $CDCl_3$) δ 199.3, 142.5, 128.6, 128.5, 126.0, 95.8, 39.5, 35.9, 31.3, 28.7, 23.5, 23.3, 10.6 ppm; IR $\nu_{max}$ ($cm^{-1}$) 2922, 2855, 1730, 1559, 1454, 1363, 1030, 747, 699; HRMS (FAB) calcd for $C_{15}H_{21}NO_3$ ($MNa^+$) 286.1414, found 286.1410.

4-nitro-10-phenyldecan-5-one

6-Phenylhexanoic acid (0.100 g, 0.52 mmol) and CDI (0.169 g, 1.04 mmol) were added together and then reacted with nitrobutane (0.080 g, 0.78 mmol) and DBU (0.198 g, 1.30 mmol) according to the general procedure. Purification by column chromatography gave 0.084 g (59%) as a yellow oil: $^1$H NMR (400 MHz, $CDCl_3$) δ 7.30 (m, 2H), 7.20 (m, 3H), 5.17 (dd, J=4.4, 10.0 Hz, 1H), 2.63 (m, 4H), 1.65 (m, 6H), 1.36 (m, 4H) 1.00 (t, J=7.2 Hz, 3H) ppm; $^{13}$C NMR (100 MHz, $CDCl_3$) δ 199.5, 142.6, 128.7, 128.6, 126.0, 94.3, 39.5, 35.9, 31.8, 31.4, 28.7, 23.3, 19.5, 13.6 ppm; IR $\nu_{max}$ ($cm^{-1}$) 3027, 2935, 2858, 1730, 1560, 1454, 1373, 1031, 749, 700; HRMS (FAB) calcd for $C_{16}H_{23}NO_3$ ($MNa^+$) 300.1570, found 300.1575.

7-nitro-1-phenylundecan-6-one

6-Phenylhexanoic acid (0.100 g, 0.52 mmol) and CDI (0.169 g, 1.04 mmol) were added together and then reacted with nitropentane (0.091 g, 0.78 mmol) and DBU (0.198 g, 1.30 mmol) according to the general procedure. Purification by column chromatography gave 0.049 g (32%) as a yellow oil: $^1$H NMR (400 MHz, $CDCl_3$) δ 7.28 (m, 2H), 7.17 (m, 3H), 5.10 (dd, J=4.4, 10.0 Hz, 1H), 2.61 (m, 4H), 1.63 (m, 6H), 1.35 (m, 6H) 0.92 (t, J=6.8 Hz, 3H) ppm; $^{13}$C NMR (100 MHz, $CDCl_3$) δ 199.5, 142.5, 128.5, 126.0, 94.5, 39.5, 35.9, 31.3, 29.6, 28.7, 28.1, 23.3, 22.2, 13.9 ppm; IR ν$_{max}$ (cm$^{-1}$) 3027, 2931, 2859, 1731, 1559, 1454, 1363, 1030, 748, 700; HRMS (FAB) calcd for C$_{17}$H$_{25}$NO$_3$ (MNa$^+$) 314.1727, found 314.1722.

7-nitro-1-phenyldodecan-6-one

6-Phenylhexanoic acid (0.150 g, 0.78 mmol) and CDI (0.253 g, 1.56 mmol) were added together and then reacted with nitrohexane (0.153 g, 1.17 mmol) and DBU (0.297 g, 1.95 mmol) according to the general procedure. Purification by column chromatography gave 0.090 g (38%) as a yellow oil: $^1$H NMR (400 MHz, CDCl$_3$) δ 7.28 (m, 2H), 7.17 (m, 3H), 5.11 (dd, J=4.8, 10.4 Hz, 1H), 2.61 (m, 4H), 1.63 (m, 6H), 1.33 (m, 8H) 0.90 (t, J=6.8 Hz, 3H) ppm; $^{13}$C NMR (100 MHz, CDCl$_3$) δ 199.5, 142.5, 128.6, 128.5, 126.0, 94.6, 39.5, 35.9, 31.3, 31.2, 29.9, 28.7, 25.7, 23.3, 22.4, 14.1 ppm; IR ν$_{max}$ (cm$^{-1}$) 3027, 2930, 2858, 1731, 1559, 1454, 1363, 1030, 748, 699; HRMS (FAB) calcd for C$_{18}$H$_{27}$NO$_3$ (MNa$^+$) 328.1883, found 328.1881.

7-nitro-1-phenyltridecan-6-one

6-Phenylhexanoic acid (0.150 g, 0.78 mmol) and CDI (0.253 g, 1.56 mmol) were added together and then reacted with nitroheptane (0.170 g, 1.17 mmol) and DBU (0.297 g, 1.95 mmol) according to the general procedure. Purification by column chromatography gave 0.104 g (42%) as a yellow oil: $^1$H NMR (400 MHz, CDCl$_3$) δ 7.28 (m, 2H), 7.17 (m, 3H), 5.11 (dd, J=4.8, 10.0 Hz, 1H), 2.61 (m, 4H), 1.63 (m, 6H), 1.33 (m, 10H) 0.89 (t, J=7.2 Hz, 3H) ppm; $^{13}$C NMR (100 MHz, CDCl$_3$) δ 199.5, 142.5, 128.6, 128.5, 126.0, 94.6, 39.4, 35.9, 31.5, 31.3, 29.9, 28.8, 28.7, 26.0, 23.3, 22.7, 14.2 ppm; IR ν$_{max}$ (cm$^{-1}$) 3027, 2931, 2859, 1731, 1559, 1454, 1363, 1031, 748, 700; HRMS (FAB) calcd for C$_{19}$H$_{29}$NO$_3$ (MNa$^+$) 342.2040, found 342.2038.

General Procedure for 2-aminoimidazole Synthesis

The appropriate α-nitro ketone (>85% pure, judged by $^1$H NMR) was dissolved in ethanol (3 mL), concentrated HCl and 5% palladium on carbon (0.2 equivalents) were added and the reaction was stirred under H$_2$ for 24 hours. The mixture was filtered through celite and the solvent was evaporated under reduced pressure. The residue was dissolved in ethanol (3 mL) and the pH was adjusted to 4.5 with 0.1 N NaOH. To the solution was added cyanamide and heated at 95° C. for 2 hours. The ethanol was then evaporated under reduced pressure and the resulting residue was purified by column chromatography (CH$_2$Cl$_2$/MeOH sat. NH$_3$ 80:20) to afford the desired compound in its free base form. Addition of concentrated HCl to a methanol solution (2 mL) of the free base followed by solvent evaporation under reduced pressure delivered the corresponding 2-aminoimidazole as its HCl salt.

5-methyl-4-(5-phenylpentyl)-1H-imidazol-2-amine (11)

2-Nitro-8-phenyloctan-3-one (0.025 g, 0.10 mmol) reacted with concentrated HCl (0.50 mmol) and palladium, 5 wt. % on activated carbon (0.043 g, 0.020 mmol) under H$_2$, then reacted with cyanamide (0.021 g, 0.50 mmol) according to the general procedure. Purification by column chromatography gave 0.010 g (41%) over two steps as a yellow oil: $^1$H NMR (300 MHz, CD$_3$OD) δ 7.22 (m, 2H), 7.14 (m, 3H), 2.59 (t, J=7.5 Hz, 2H), 2.42 (t, J=6.9 Hz, 2H), 2.01 (s, 3H) 1.60 (m, 4H), 1.31 (m, 2H) ppm; $^{13}$C NMR (75 MHz, CD$_3$OD) δ 146.2, 142.5, 128.3, 128.1, 125.5, 121.9, 117.5, 35.5, 31.1, 28.6, 28.1, 22.9, 7.5 ppm; IR ν$_{max}$ (cm$^{-1}$) 3169, 2929, 2857, 1680, 1453, 1020, 749, 700; HRMS (FAB) calcd for C$_{15}$H$_{21}$N$_3$ (MH$^+$) 244.1808, found 244.1814.

5-ethyl-4-(5-phenylpentyl)-1H-imidazol-2-amine (12)

3-Nitro-9-phenylnonan-4-one (0.050 g, 0.19 mmol) reacted with concentrated HCl (0.95 mmol) and palladium, 5 wt. % on activated carbon (0.081 g, 0.038 mmol) under H$_2$, then reacted with cyanamide (0.040 g, 0.95 mmol) according to the general procedure. Purification by column chromatography gave 0.014 g (29%) over two steps as a yellow oil: $^1$H NMR (300 MHz, CD$_3$OD) δ 7.25 (m, 2H), 7.14 (m, 3H), 2.59 (t, J=7.5 Hz, 2H), 2.42 (m, 4H), 1.63 (m, 4H), 1.28 (m, 2H), 1.13 (t, J=7.5 Hz, 3H) ppm; $^{13}$C NMR (75 MHz, CD$_3$OD) δ 146.2, 142.4, 128.2, 128.1, 125.5, 123.6, 121.3, 35.5, 31.1, 28.7, 28.1, 22.9, 16.5, 13.1 ppm; IR ν$_{max}$ (cm$^{-1}$) 3327, 2934, 1680, 1453, 1016, 749; HRMS (FAB) calcd for C$_{16}$H$_{23}$N$_3$ (MH$^+$) 258.1965, found 258.1973.

4-(5-phenylpentyl)-5-propyl-1H-imidazol-2-amine (13)

4-Nitro-10-phenyldecan-5-one (0.084 g, 0.30 mmol) reacted with concentrated HCl (1.50 mmol) and palladium, 5 wt. % on activated carbon (0.129 g, 0.060 mmol) under H$_2$, then reacted with cyanamide (0.064 g, 1.50 mmol) according to the general procedure. Purification by column chromatography gave 0.025 g (30%) over two steps as a yellow oil: $^1$H NMR (300 MHz, CD$_3$OD) δ 7.20 (m, 2H), 7.15 (m, 3H), 2.60 (t, J=7.2 Hz, 2H), 2.40 (m, 4H), 1.56 (m, 6H), 1.30 (m, 2H), 0.92 (t, J=7.2 Hz, 3H) ppm; $^{13}$C NMR (100 MHz, CD$_3$OD) δ 146.4, 142.5, 128.3, 128.1, 125.6, 122.1, 121.9, 35.5, 31.1, 28.8, 28.2, 25.0, 23.0, 22.3, 12.6 ppm; IR ν$_{max}$ (cm$^{-1}$) 3165, 2931, 1680, 1453, 1031, 747, 699; HRMS (FAB) calcd for C$_{17}$H$_{25}$N$_3$ (MH$^+$) 272.2121, found 272.2127.

5-butyl-4-(5-phenylpentyl)-1H-imidazol-2-amine (14)

7-Nitro-1-phenylundecan-6-one (0.049 g, 0.17 mmol) reacted with concentrated HCl (0.85 mmol) and palladium, 5 wt. % on activated carbon (0.072 g, 0.034 mmol) under H$_2$, then reacted with cyanamide (0.035 g, 0.84 mmol) according to the general procedure. Purification by column chromatography gave 0.025 g (52%) over two steps as a yellow oil: $^1$H NMR (400 MHz, CD$_3$OD) δ 7.22 (m, 2H), 7.15 (m, 3H), 2.60 (t, J=7.2 Hz, 2H), 2.43 (m, 4H), 1.64 (m, 6H), 1.34 (m, 4H), 0.94 (t, J=7.6 Hz, 3H) ppm; $^{13}$C NMR (75 MHz, CD$_3$OD) δ 146.4, 142.4, 128.2, 128.1, 125.6, 122.1, 121.9, 35.5, 31.2, 31.1, 28.7, 28.2, 23.0, 22.8, 21.9, 12.9 ppm; IR ν$_{max}$ (cm$^{-1}$) 3166, 2930, 2857, 1680, 1453, 1030, 748, 699; HRMS (FAB) calcd for C$_{18}$H$_{27}$N$_3$ (MH$^+$) 286.2278, found 286.2288.

5-pentyl-4-(5-phenylpentyl)-1H-imidazol-2-amine (15)

7-Nitro-1-phenyldodecan-6-one (0.090 g, 0.29 mmol) reacted with concentrated HCl (1.45 mmol) and palladium, 5 wt. % on activated carbon (0.125 g, 0.060 mmol) under H$_2$, then reacted with cyanamide (0.062 g, 1.47 mmol) according to the general procedure. Purification by column chromatography gave 0.071 g (81%) over two steps as a yellow oil: $^1$H NMR (300 MHz, CD$_3$OD) δ 7.20 (m, 2H), 7.14 (m, 3H), 2.59 (t, J=7.5 Hz, 2H), 2.42 (m, 4H), 1.56 (m, 6H), 1.32 (m, 6H), 0.90 (t, J=7.2 Hz, 3H) ppm; $^{13}$C NMR (75 MHz, CD$_3$OD) δ 146.3, 142.5, 128.3, 128.1, 125.6, 122.1, 121.8, 35.5, 31.1, 31.1, 28.7, 28.7, 28.2, 23.1, 23.0, 22.3, 13.3 ppm; IR ν$_{max}$ (cm$^{-1}$) 3169, 2928, 2857, 1680, 1453, 1202, 1030, 746, 699; HRMS (FAB) calcd for C$_{19}$H$_{29}$N$_3$ (MH$^+$) 300.2434, found 300.2441.

5-hexyl-4-(5-phenylpentyl)-1H-imidazol-2-amine (19)

7-Nitro-1-phenyltridecan-6-one (0.104 g, 0.33 mmol) reacted with concentrated HCl (1.65 mmol) and palladium, 5 wt. % on activated carbon (0.139 g, 0.065 mmol) under H$_2$, then reacted with cyanamide (0.068 g, 1.63 mmol) according to the general procedure. Purification by column chromatography gave 0.049 g (48%) over two steps as a yellow oil: $^1$H NMR (400 MHz, CD$_3$OD) δ 7.23 (m, 2H), 7.15 (m, 3H), 2.60 (t, J=7.6 Hz, 2H), 2.42 (m, 4H), 1.63 (m, 6H), 1.30 (m, 8H), 0.89 (t, J=6.8 Hz, 3H) ppm; $^{13}$C NMR (100 MHz, CD$_3$OD) δ 146.4, 142.4, 128.2, 128.1, 125.6, 122.1, 121.8, 35.5, 31.5, 31.1, 29.0, 28.7, 28.6, 28.2, 23.1, 23.0, 22.5, 13.3 ppm; IR ν$_{max}$ (cm$^{-1}$) 3165, 2929, 2857, 1680, 1453, 1202, 1029, 747, 699; HRMS (FAB) calcd for C$_{20}$H$_{31}$N$_3$ (MH$^+$) 314.2591, found 314.2596.

Control 2-aminoimidazole Synthesis 22 and 23 were synthesized from their corresponding carboxylic acids as outlined below, using established literature protocols (Richards et al., *Org. Biomol. Chem.,* 2008, 6: 1356-1363).

1-bromooctan-2-one

To a 100 mL round bottomed flask, heptanoic acid (1.41 g, 10.81 mmol) was added and then dissolved in dichloromethane and a stir bar was added and allowed to stir. Then, three drops of dimethylformamide was added and then the reaction mixture was cooled to 0° C. Oxalyl chloride (4.12 g, 32.43 mmol) was added dropwise and left to continue stirring for one hour. Separately in a diazomethane kit, a stir bar, KOH (10.00 g, 178.2 mmol), 24 mL of ethanol, 17 mL of water was added to the top of the diazomethane apparatus and was heated to 65° C. and stirred. To a diazomethane kit liquid addition funnel diazald (10.00 g, 46.67 mmol) and 100 mL of diethyl ether was added. The diethyl ether/diazald mixture was allowed to add dropwise to the KOH/water/ethanol mixture so that the diazomethane was generated and distilled over to the collection flask that was cooled to 0° C. Once the diazomethane had been completely collected, and the heptanoic acid had reacted with the oxalyl chloride for one hour, the heptanoic acid reaction mixture was concentrated in vacuo without heating in excess of 25° C., dissolved in 3 mL of dichloromethane and was added slowly to the flask containing the diazomethane while still being cooled to 0° C. The reaction mixture was allowed to stir for one hour at 0° C. Then 4 mL of concentrated hydrobromic acid was added slowly to the reaction mixture and allowed to stir for 20 minutes. Then, 100 mL of a saturated sodium bicarbonate solution was added slowly to the reaction mixture and allowed to stir for 30 minutes. The resulting mixture was then extracted with ethyl acetate, washed twice with a brine solution, concentrated in vacuo and then purified via column chromatography with a 10% ethyl acetate/hexanes solution providing 1-bromooctan-2-one as a light yellow oil (2.19 g, 97% yield) $^1$H NMR (300 MHz, CDCl$_3$) δ 3.79 (s, 2H), δ 2.49 (t, J=7.2 Hz, 2H), δ 1.44 (m, 2H), δ 1.13 (bs, 6H), δ 0.72 (t, J=4.5 Hz, 3H) ppm; $^{13}$C NMR (75 MHz, CDCl$_3$) δ 202.15, 39.9, 34.9, 31.6, 28.8, 23.9, 22.6, 14.1 ppm; IR ν$_{max}$ (cm$^{-1}$) 3423, 306, 3025, 2933, 2856, 1716, 1495, 1453, 1030, 748; HRMS (ESI) calcd for C$_8$H$_{15}$$^{79}$BrO (M+) 206.0306, found 206.0301.

1-bromo-7-phenylhexan-2-one

To a 100 mL round bottomed flask, phenyl hexanoic acid (2.08 g, 10.81 mmol) was added and then dissolved in dichloromethane and a stir bar was added and allowed to stir. Then, three drops of dimethylformamide was added and then the reaction mixture was cooled to 0° C. Oxalyl chloride (4.12 g, 32.43 mmol) was added dropwise and left to continue stirring for one hour. Separately in a diazomethane kit, a stir bar, KOH (10.00 g, 178.2 mmol), 24 mL of ethanol, 17 mL of water was added to the top of the diazomethane apparatus and was heated to 65° C. and stirred. To a diazomethane kit liquid addition funnel diazald (10.00 g, 46.67 mmol) and 100 mL of diethyl ether was added. The diethyl ether/diazald mixture was allowed to add dropwise to the KOH/water/ethanol mixture so that the diazomethane was generated and distilled over to the collection flask that was cooled to 0° C. Once the diazomethane had been completely collected, and the heptanoic acid had reacted with the oxalyl chloride for one hour, the heptanoic acid reaction mixture was concentrated in vacuo without heating in excess of 25° C., dissolved in 3 mL of dichloromethane and was added slowly to the flask containing the diazomethane while still being cooled to 0° C. The reaction mixture was allowed to stir for one hour at 0° C. Then 4 mL of concentrated hydrobromic acid was added slowly to the reaction mixture and allowed to stir for 20 minutes. Then, 100 mL of a saturated sodium bicarbonate solution was added slowly to the reaction mixture and allowed to stir for 30 minutes. The resulting mixture was then extracted with ethyl acetate, washed twice with a brine solution, concentrated in vacuo and then purified via column chromatography with a 10% ethyl acetate/hexanes solution providing 1-bromo-7-phenylheptan-2-one as a light yellow oil (2.53 g, 87% yield). $^1$H NMR (300 MHz, CDCl$_3$) δ 7.32 (t, J=7.5 Hz, 2H), δ 7.20 (d, J=7.5 Hz, 3H), δ 3.86 (s, 2H), 62.63 (t, J=7.2 Hz, 4H), δ 1.65 (q, J=7.8, 7.2 Hz, 4H), δ 1.34 (m, 2H) ppm; $^{13}$C NMR (75 MHz, CDCl$_3$) δ 202.3, 142.7, 128.7, 128.6, 126.0, 39.9, 35.9, 34.9, 31.5, 28.9, 23.8 ppm; IR ν$_{max}$ (cm$^{-1}$) 3434, 2930, 2848, 2113, 1641, 1393; HRMS (ESI) calcd for C$_{13}$H$_{17}$$^{79}$BrO (M+) 268.0462, found 268.0467.

4-hexyl-1H-imidazol-2-amine hydrochloride 1-bromooctan-2-one (1.00 g, 4.83 mmol) was placed in a 50 mL round bottomed flask with a stir bar and dissolved in 10 mL of DMF. Boc guanidine (2.31 g, 14.89 mmol) was then added to the reaction mixture and it was allowed to stir for 48 hours. Water was then added to the reaction mixture and it was placed in a separatory funnel. The mixture was then extracted twice with ethyl acetate, washed twice with water, washed twice with brine, concentrated de vacuo and then purified via column chromatography (5% methanol/ 95% dichloromethane) to provide tert-butyl 2-amino-4-hexyl-1H-imidazole-1-carboxylate as a hygroscopic light yellow solid (0.74 g, 57% yield). $^1$H NMR (300 MHz, CDCl$_3$) δ 6.69 (s, 2H), δ 6.34 (s, 1H), δ 2.20 (t, J=7.5 Hz, 2H), δ 1.44 (bs, 11H), 1.17 (s, 6H), δ 0.76 (s, 3H) ppm; $^{13}$C NMR (75 MHz, CDCl$_3$) δ 151.1, 149.6, 139.3, 105.7, 84.1, 31.8, 29.2, 28.4, 28.3, 28.0, 22.7, 14.2 ppm; IR $v_{max}$ (cm$^{-1}$) 3421, 2109, 1644, 1442, 1204, 1142; HRMS (ESI) calcd for $C_{14}H_{25}N_3O_2$ (M+) 267.1946, found 267.1940. Then, tert-butyl 2-amino-4-hexyl-1H-imidazole-1-carboxylate was dissolved in a 1:4 mixture of trifluoroacetic acid/dichloromethane and allowed to stir for five hours and then concentrated de vacuo. The sample was then dissolved with a dilute HCl/methanol (5 drops HCl/50 mL of methanol) and then concentrated in vacuo to provide 4-(5phenylpentyl)-1H)-imidazol-2-amine hydrochloride as a hygroscopic light yellow solid (0.57 g, 57% overall yield). $^1$H NMR (300 MHz, CD$_3$OD) δ 6.34 (bs, 3H), δ 2.41 (t, J=7.5 Hz, 2H), δ1.56 (m, 2H), δ 1.28 (bs, 6H), δ 0.82 (t, J=6.6 Hz, 3H) ppm; $^{13}$C NMR (75 MHz, CDCl$_3$) δ 151.4, 131.9, 111.9, 35.3, 32.4, 31.9, 28.3, 26.3, 17.1 ppm; IR $v_{max}$ (cm$^{-1}$) 3411, 2099, 1638; HRMS (ESI) calcd for $C_9H_{17}N_3$ (M+) 167.1422, found 167.1416.

4-(5phenylpentyl)-1H)-imidazol-2-amine hydrochloride 1-bromo-7-phenylheptan-2-one (1.00 g, 3.71 mmol) was placed in a 50 mL round bottomed flask with a stir bar and dissolved in 10 mL of DMF. Boc guanidine (1.77 g, 11.13 mmol) was then added to the reaction mixture and it was allowed to stir for 48 hours. Water was then added to the reaction mixture and it was placed in a separatory funnel. The mixture was then extracted twice with ethyl acetate, washed twice with water, washed twice with brine, concentrated de vacuo and then purified via column chromatography (5% methanol/95% dichloromethane) to provide tert-butyl 2-amino-4-(5-phenylpentyl)-1H-imidazole-1-carboxylate as a hygroscopic light yellow solid (0.77 g, 63% yield). $^1$H NMR (300 MHz, CDCl$_3$) δ 7.31 (m, 2H), δ 7.26 (m, 3H), δ 6.66 (s, 2H), δ 6.51 (s, 1H), δ 2.63 (t, J=7.5 Hz, 2H), δ 2.39 (t, J=7.5 Hz, 2H), δ 1.67 (m, 4H), δ 1.53 (s, 9H), δ 1.40 (m, 2H) ppm; $^{13}$C NMR (75 MHz, CDCl$_3$) δ 151.1, 149.8, 143.0, 130.3, 128.7, 128.5, 125.8, 106.2, 84.5, 36.1, 31.6, 29.2, 28.5, 28.4, 28.2 ppm; IR $v_{max}$ (cm$^{-1}$) 3433, 2098, 1639, 1454, 1204; HRMS (ESI) calcd for $C_{19}H_{27}N_3O_2$ (M+) 329.2103, found 329.2109. Then, tert-butyl 2-amino-4-(5-phenylpentyl)-1H-imidazole-1-carboxylate was dissolved in a 1:4 mixture of trifluoroacetic acid/dichloromethane and allowed to stir for five hours and then concentrated de vacuo. The sample was then dissolved with a dilute HCl/methanol (5 drops HCl/50 mL of methanol) and then concentrated de vacuo to provide 4-(5phenylpentyl)-1H)-imidazol-2-amine hydrochloride as a hygroscopic light yellow solid (0.62 g, 63% overall yield). $^1$H NMR (300 MHz, CD$_3$OD) δ 7.20 (t, J=7.2 Hz, 2H), δ 7.12 (d, J=7.2 Hz, 3H), δ 6.37 (s, 1H), δ 2.56 (t, J=7.5 Hz, 2H), δ 2.41 (t, J=7.5 Hz, 2H), δ 1.57 (m, 4H), δ 1.34 (m, 2H) ppm; $^{13}$C NMR (75 MHz, CDCl$_3$) 147.3, 142.5, 128.3, 128.1, 127.7, 125.6, 108.2, 35.5, 31.1, 28.3, 27.0, 24.2 ppm; IR $v_{max}$ (cm$^{-1}$) 3385, 2933, 2857, 1679, 1536, 1495, 1453, 1335, 1172, 748, 700; HRMS (ESI) calcd for $C_{14}H_{19}N_3$(M+) 229.1578, found 229.1571.

Biological Screening Experimental

Broth Microdilution Method for MIC Determination.

Overnight cultures of bacterial strain were subcultured to 5×10$^5$ CFU/mL in Mueller-Hinton medium (Fluka #70192). The resulting bacterial suspension was aliquoted (1.0 mL) into culture tubes. Samples were prepared from these culture tubes containing either 256 μg/mL of specified antibiotic or no test compound as a control. Samples were then aliquoted (200 μL) into the first row of wells of a 96-well microtiter plate in which subsequent wells were prefilled with 100 μL of Mueller-Hinton medium based 5×10$^5$ CFU/mL bacterial subculture. Using the multichannel pipettor set at 100 μL, row one wells were mixed 8-10 times. Then, 100 μL were withdrawn and transferred to row two. Row two wells were mixed 8-10 times followed by a 100 μL transfer from row two to row three. This procedure was used to serial dilute the rest of the rows of the microtiter plate. The microtiter plate sample was then covered with a microtiter plate lid and then placed in a covered plastic container. The chamber was incubated under stationary conditions at 37° C. After 16 hours, the lid was removed and MIC values were recorded.

Red Blood Cell Hemolysis Assay.

Hemolysis assays were performed on mechanically difibrinated sheep blood (Hemostat Labs: DSB100). 1.5 mL of blood was placed into a microcentrifuge tube and centrifuged at 10000 rpm for ten minutes. The supernatant was removed and then the cells were resuspended with 1 mL of phosphate-buffered saline (PBS). The suspension was centrifuged, the supernatant was removed and cells resuspended two more times. The final cell suspension was then diluted tenfold. Test compound solutions were made in PBS and then added to aliquots of the tenfold suspension dilution. PBS alone was used as a negative control and as a zero hemolysis marker whereas a 1% Triton X sample was used as a positive control and the 100% lysis marker. Samples were then placed in an incubator at 37° C. while being shaken at 200 rpm for one hour. After one hour, the samples were transferred to microcentrifuge tubes and then centrifuged at 10000 rpm for ten minutes. The resulting supernatant was diluted by a factor of 40 in distilled water. The absorbance of the supernatant was measured with a UV spectrometer at a 540 nm wavelength.

Procedure to Determine the Dispersal Effect of Test Compounds on E. faecium (VRE), MRSA, S. aureus, S. epidermidis, E. coli, R. salexigens, V. cholerae, V. vulnificus and L. anguillarum Preformed Biofilms: Dispersion assays were performed by taking an overnight culture of bacterial strain and subculturing it at an OD$_{600}$ of 0.01 into the necessary medium (brain heart infusion for E. faecium, tryptic soy broth with a 0.5% glucose supplement (TSBG) for MRSA, S. aureus and S. epidermidis, Luria-Bertani (LB) medium for MDRAB and E. coli, and tryptic soy broth with a 0.5% glucose supplement and a 3.0% NaCl supplement (TGN) for R. salexigens, V. cholerae, V. vulnificus and L. anguillarum.) The resulting bacterial suspension was aliquoted (100 μL) into the wells of a 96-well PVC microtiter plate. Plates were then wrapped in GLAD Press n' Seal® followed by an incubation under stationary conditions at 37° C. to establish the biofilms. After 24 h, the medium was discarded from the wells and the plates were washed thoroughly with water. Stock solutions of predetermined concentrations of the test compound were then made in the necessary medium. These stock solutions were aliquoted (100 μL) into the wells of the 96-well PVC microtiter plate with the established biofilms. Medium alone was added to a subset of the wells to serve as a control. Sample plates were then incubated for 24 h at 37° C. After incubation, the medium was discarded from the wells and the plates were washed thoroughly with water. Plates were then stained with 100 μL of 0.1% solution of crystal violet (CV) and then incubated at ambient temperature for 30 min. Plates were washed with water again and the remaining stain was solubilized with 200 μL of 95% ethanol. A sample of 125 μL of solubilized CV stain from each well was transferred to the corresponding wells of a polystyrene microtiter dish. Biofilm dispersion was quantitated by measuring the $OD_{540}$ of each well in which a negative control lane wherein no biofilm was formed served as a background and was subtracted out.

EXAMPLE 2

Activity Testing of First and Second Generation Library Members on Plant or Plant Part Pathogens A standard crystal violet reporter assay is employed to assess the effect of compounds from the libraries reported above in Example 1 on the formation or dispersion of biofilms and/or microbial growth (e.g., bacterial strains, fungal strains, etc.) on plants or plant parts.

The foregoing is illustrative of the present invention, and is not to be construed as limiting thereof. The invention is defined by the following claims, with equivalents of the claims to be included therein.

That which is claimed is:

1. A compound of Formula (I)(a):

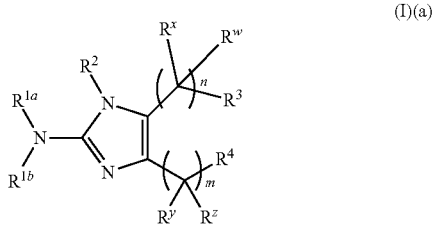

wherein:
$R^{1a}$, $R^{1b}$ and $R^2$ are each H;
n=3 to 7;
m=0;
$R^3$ and $R^4$ are each aryl; and
each occurrence of $R^w$, $R^x$, $R^y$ and $R^z$ is H,
or a salt thereof.

2. The compound of claim 1, wherein said compound has microbicidal activity.

3. A composition comprising a carrier and an effective amount of the compound of claim 1.

4. The composition of claim 3, wherein said composition is formulated for topical use.

5. The composition of claim 3, wherein said composition is an ointment, cream, lotion, paste, gel, spray, aerosol, or oil.

6. A composition comprising the compound of claim 1 covalently coupled to a substrate.

7. A biofilm or bacterial growth inhibiting coating composition, comprising:
   (a) a film-forming resin;
   (b) a solvent that disperses said resin;
   (c) an effective amount of the compound of claim 1, wherein said effective amount of said compound inhibits the growth of a biofilm and/or bacteria thereon; and
   (d) optionally, at least one pigment.

8. The compound of claim 1, wherein $R^3$ and $R^4$ are each phenyl.

9. The compound of claim 8, wherein n=5.

10. A composition comprising a carrier and an effective amount of the compound of claim 9.

11. A composition comprising the compound of claim 9 covalently coupled to a substrate.

12. A method of controlling biofilm formation or microbial growth on a substrate comprising the step of contacting the compound of claim 1 to said substrate in an amount effective to inhibit biofilm formation or microbial growth.

13. The method of claim 12, wherein said method comprises the step of clearing a preformed biofilm from said substrate by administering an effective amount of the compound to said substrate, wherein said effective amount will reduce the amount of said biofilm on said substrate.

14. A method for treating a chronic bacterial infection in a subject in need thereof, comprising administering to said subject the compound of claim 1 in an amount effective to inhibit, reduce, or remove a biofilm component of said chronic bacterial infection.

15. The method of claim 14, wherein said chronic bacterial infection is selected from the group consisting of urinary tract infection, gastritis, respiratory infection, cystitis, pyelonephritis, osteomyelitis, bacteremia, skin infection, rosacea, acne, chronic wound infection, infectious kidney stones, bacterial endocarditis, and sinus infection.

16. A medical device comprising:
   (a) a medical device substrate; and
   (b) an effective amount of the compound of claim 1, either coating the substrate, or incorporated into the substrate, wherein said effective amount of said compound inhibits the growth of a biofilm and/or bacteria thereon.

17. A method of preventing, removing or inhibiting microbial biofilm formation or microbial infection in a plant or plant part thereof, comprising applying to said plant or plant part a treatment effective amount of a compound of claim 1, or an agriculturally acceptable salt thereof.

18. The method of claim 17, wherein said plant is a fruit crop plant or a vegetable crop plant.

19. The method of claim 17, wherein said microbial biofilm formation or microbial infection is caused by a fungi.

20. The method of claim 17, wherein said compound is applied to said plant in an amount effective to treat or control a fungal disease selected from the group consisting of rots, leaf molds, blights, wilts, damping-off, spot, root rot, stem rot, mildew, brown spot, gummosis, melanose, post-bloom fruit drop, scab, alternaria, canker, flyspeck, fruit blotch, dieback, downy mildews, ear rots, anthracnose bunts, smut, rust, eyespot and pecky rice.

21. A method of enhancing the effects of a fungicide, comprising applying the compound of claim 1 in combination with said fungicide.

22. The method of claim 21, wherein said fungicide comprises copper.

23. The method of claim 21, wherein said fungicide and said compound are applied simultaneously.

24. The method of claim 21, wherein said fungicide and said compound are applied sequentially.

25. The method of claim 21, wherein said applying is carried out on a plant or plant part.

26. A method of controlling biofilm formation or microbial growth on a substrate comprising the step of contacting the compound of claim 9 to said substrate in an amount effective to inhibit biofilm formation or microbial growth.

* * * * *